(12) United States Patent
McDaniel et al.

(10) Patent No.: US 7,444,722 B2
(45) Date of Patent: Nov. 4, 2008

(54) REFASTENABLE ABSORBENT GARMENT

(75) Inventors: Mary Lou McDaniel, Appleton, WI (US); Nadezhda Efremova, Neenah, WI (US); Joseph Earl Pierce, Appleton, WI (US); Lisha Yu, Appleton, WI (US); Brian Van Benschoten, Newmarket, NH (US); Wallace L. Kurtz, Jr., Lunenburg, MA (US); Ernesto S. Tachauer, Bedford, NH (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 28 days.

(21) Appl. No.: 11/262,009

(22) Filed: Oct. 28, 2005

(65) Prior Publication Data
US 2006/0090307 A1 May 4, 2006

Related U.S. Application Data

(63) Continuation-in-part of application No. 10/837,346, filed on Apr. 30, 2004.

(51) Int. Cl.
*A61F 13/62* (2006.01)
*A44B 18/00* (2006.01)

(52) U.S. Cl. .................. 24/446; 24/452; 604/385.03; 604/387; 604/391

(58) Field of Classification Search .............. 24/442, 24/450, 452, 446; 604/387, 391, 385.03, 604/385.04
See application file for complete search history.

(56) References Cited

U.S. PATENT DOCUMENTS

| | | |
|---|---|---|
| 3,261,069 A | 7/1966 | Mathison |
| 3,338,992 A | 8/1967 | Kinney |
| 3,341,394 A | 9/1967 | Kinney |
| 3,408,705 A | 11/1968 | Kayser et al. |
| 3,502,538 A | 3/1970 | Petersen |
| 3,502,763 A | 3/1970 | Hartman |
| 3,542,615 A | 11/1970 | Dobo et al. |
| 3,692,618 A | 9/1972 | Dorschner et al. |

(Continued)

FOREIGN PATENT DOCUMENTS

EP 0 276 970 A2 8/1988

(Continued)

OTHER PUBLICATIONS

American Society for Testing Materials (ASTM) Designation: D 790-99, "Standard Test Methods for Flexural Properties of Unreinforced and Reinforced Plastics and Electrical Insulating Materials," pp. 150-158, published Feb. 2000.

(Continued)

*Primary Examiner*—James R Brittain
(74) *Attorney, Agent, or Firm*—Gregory E. Croft; Patricia A. Charlier; Sebastian C. Pugliese, II

(57) ABSTRACT

A male component of a mechanical fastening system, such as a hook and loop fastener, that can remain fastened to a female component under high levels of shear force. The male component has a backing material with protrusions extending from the backing material at an angle toward the direction of fastener force. The combination of the male component with a female loop component results in a secure fastening system.

15 Claims, 13 Drawing Sheets

U.S. PATENT DOCUMENTS

| | | | |
|---|---|---|---|
| 3,717,908 A | 2/1973 | Perina | |
| 3,802,817 A | 4/1974 | Matsuki et al. | |
| 3,849,241 A | 11/1974 | Butin et al. | |
| 3,921,259 A | 11/1975 | Brumlik | |
| 4,056,593 A | 11/1977 | De Navas Albareda | |
| 4,340,563 A | 7/1982 | Appel et al. | |
| 4,680,838 A | 7/1987 | Astl | |
| 4,794,028 A | 12/1988 | Fischer | |
| 4,794,674 A | 1/1989 | Mintel et al. | |
| 4,842,916 A | 6/1989 | Ogawa et al. | |
| 4,846,815 A | 7/1989 | Scripps | |
| 4,946,527 A | 8/1990 | Battrell | |
| 4,984,339 A | 1/1991 | Provost et al. | |
| 5,019,073 A | 5/1991 | Roessler et al. | |
| 5,058,247 A | 10/1991 | Thomas et al. | |
| 5,067,210 A | 11/1991 | Keyaki | |
| 5,116,563 A | 5/1992 | Thomas et al. | |
| 5,208,952 A | 5/1993 | Mintel et al. | |
| 5,260,015 A | 11/1993 | Kennedy et al. | |
| 5,300,058 A * | 4/1994 | Goulait et al. | 604/391 |
| 5,318,555 A | 6/1994 | Siebers et al. | |
| 5,325,569 A | 7/1994 | Goulait et al. | |
| 5,374,262 A | 12/1994 | Keuhn, Jr. et al. | |
| 5,383,872 A | 1/1995 | Roessler et al. | |
| 5,392,498 A | 2/1995 | Goulait et al. | |
| 5,398,387 A | 3/1995 | Torigoe et al. | |
| 5,470,417 A | 11/1995 | Goulait | |
| 5,518,795 A | 5/1996 | Kennedy et al. | |
| 5,537,720 A | 7/1996 | Takizawa et al. | |
| 5,540,673 A | 7/1996 | Thomas et al. | |
| 5,549,591 A | 8/1996 | Landvogt | |
| 5,586,371 A | 12/1996 | Thomas | |
| 5,676,652 A | 10/1997 | Hunter et al. | |
| 5,678,286 A | 10/1997 | Murasaki | |
| 5,692,271 A | 12/1997 | Provost et al. | |
| 5,720,740 A | 2/1998 | Thomas | |
| 5,744,080 A | 4/1998 | Kennedy et al. | |
| 5,749,849 A | 5/1998 | Engelson | |
| 5,755,015 A | 5/1998 | Akeno et al. | |
| 5,762,645 A | 6/1998 | Peck et al. | |
| 5,778,457 A | 7/1998 | Conway | |
| 5,781,969 A | 7/1998 | Akeno et al. | |
| 5,792,408 A | 8/1998 | Akeno et al. | |
| 5,813,095 A | 9/1998 | Robertson | |
| 5,851,467 A | 12/1998 | Murasaki | |
| 5,858,515 A | 1/1999 | Stokes et al. | |
| 5,875,527 A | 3/1999 | Lacey et al. | |
| 5,884,374 A | 3/1999 | Clune | |
| 5,887,320 A | 3/1999 | Provost | |
| 5,891,549 A | 4/1999 | Beretta et al. | |
| 5,897,545 A | 4/1999 | Kline et al. | |
| 5,930,876 A | 8/1999 | Takizawa et al. | |
| 5,933,927 A | 8/1999 | Miller et al. | |
| 5,942,177 A | 8/1999 | Banfield | |
| 5,945,193 A | 8/1999 | Pollard et al. | |
| 5,953,797 A | 9/1999 | Provost et al. | |
| 5,961,761 A | 10/1999 | Heindel et al. | |
| 5,964,742 A | 10/1999 | McCormack et al. | |
| 5,985,407 A | 11/1999 | Murasaki | |
| 6,000,106 A | 12/1999 | Kampfer et al. | |
| 6,054,091 A | 4/2000 | Miller et al. | |
| 6,061,881 A | 5/2000 | Takizawa et al. | |
| 6,077,255 A | 6/2000 | Hunter et al. | |
| 6,131,251 A | 10/2000 | Provost | |
| 6,180,205 B1 | 1/2001 | Tachauer et al. | |
| 6,209,177 B1 | 4/2001 | Murasaki | |
| 6,221,960 B1 | 4/2001 | Rajagopalan | |
| 6,254,304 B1 | 7/2001 | Takizawa et al. | |
| 6,276,032 B1 | 8/2001 | Nortman et al. | |
| 6,503,855 B1 | 1/2003 | Menzies et al. | |
| 6,582,411 B1 | 6/2003 | Carstens et al. | |
| 6,588,073 B1 | 7/2003 | Zoromski et al. | |
| 6,623,469 B1 | 9/2003 | Thomas | |
| 2002/0116799 A1 | 8/2002 | Martin et al. | |
| 2002/0138064 A1 | 9/2002 | Datta et al. | |
| 2003/0181884 A1 | 9/2003 | Carstens et al. | |
| 2005/0131372 A1 | 6/2005 | Wheeler et al. | |
| 2005/0131376 A1 | 6/2005 | Wheeler et al. | |
| 2005/0241119 A1 | 11/2005 | Efremova et al. | |

FOREIGN PATENT DOCUMENTS

| | | |
|---|---|---|
| EP | 0 374 730 B1 | 4/1994 |
| EP | 0 476 992 B1 | 7/1995 |
| EP | 0 766 934 A2 | 4/1997 |
| EP | 0 768 074 A1 | 4/1997 |
| EP | 0 800 379 B1 | 12/1999 |
| GB | 2 296 423 A | 7/1996 |
| WO | WO 93/00215 A1 | 1/1993 |
| WO | WO 96/19960 A1 | 7/1996 |
| WO | WO 00/50229 A1 | 8/2000 |
| WO | WO 01/67911 A2 | 9/2001 |
| WO | WO 01/68019 A1 | 9/2001 |
| WO | WO 02/14701 A2 | 2/2002 |
| ZA | 83/2380 | 11/1985 |

OTHER PUBLICATIONS

American Society for Testing Materials (ASTM) Designation: D 882-97, "Standard Test Method for Tensile Properties of Thin Plastic Sheeting," pp. 159-167, published Apr. 1998.

* cited by examiner

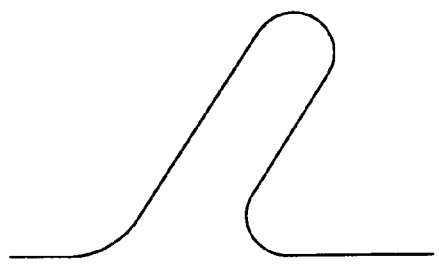
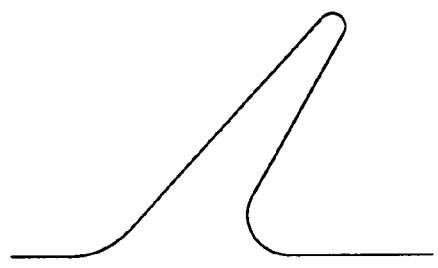
FIG. 6a  FIG. 6b
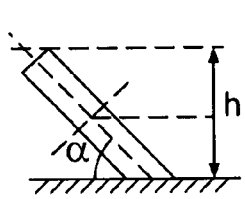
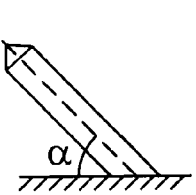
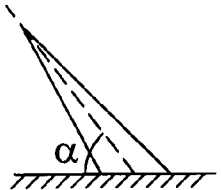
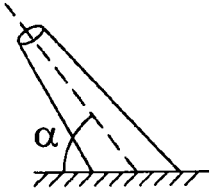
FIG. 7a  FIG. 7b  FIG. 7c  FIG. 7d
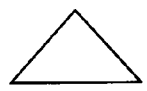
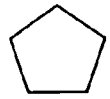
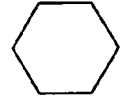
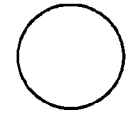
FIG. 8a  FIG. 8b  FIG. 8c  FIG. 8d
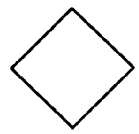
FIG. 8e  FIG. 8f  FIG. 8g Nylon:

Cotton:

Microfiber:

Satin:

REFASTENABLE ABSORBENT GARMENT

This application is a continuation-in-part of U.S. Ser. No. 10/837,346 filed Apr. 30, 2004.

BACKGROUND OF THE INVENTION

The use of fastening systems on disposable absorbent products, such as diapers, training pants, adult incontinent products, feminine care products, and the like, is well known. These fastening systems include pins, ties, buttons, snaps, adhesives, and mechanical fastening systems. Key performance requirements of such fastening systems include a balance of maintaining the position of the absorbent products during use and low/no impact on the garments that the fastening system comes into contact with or utilizes during the use of the absorbent product.

Refastenable mechanical fastening systems such as Velcro®-style hook and loop mechanical fastening systems are well known in the art. Typically, such fastening systems involve two major components, a male component and a female component that when engaged can hold two substrates together. The male component typically includes a backing material with a number of protruding hook elements that are designed to engage with a number of loops on a complimentary female component. These hook elements protruding from the backing material of the male component typically consist of a base, a shank and an engaging means in the form of a hook, a cap, a spherical/hemi-spherical shape, a flat top, etc. Generally, a loop fastening material comprises fibrous loops protruding from the backing material and is capable of engaging the above-described male component of a mechanical fastener.

When the mechanical fastening system becomes engaged, a hook element penetrates the loop fastening material and either engages or intercepts fibrous loops of the loop fastening material. This results in a mechanical interference and physical obstruction which prevent the removal of hook material from the loop material until the separation forces, usually in the form of either peel or shear forces, exceed a certain threshold. After this, the disengagement of a mechanical fastener occurs resulting in separation of the hook component and the loop component. Furthermore, the separation forces being applied to the loop material during the disengagement stage can result in loop breakage, fiber pull-out and fiber string-out, fuzzy marks on the loop material etc., up to mechanical tear of the loop material.

The common way to avoid these problems is to use a female component of a mechanical fastening system that is specifically designed to engage with a particular male component and thus possesses a necessary mechanical strength, fiber strength, fiber thickness, and/or a particular fiber bonding pattern, in order to prevent the above-mentioned problems. Examples of suitable loop materials include Velcro® brand loop materials sold by Velcro USA of Manchester, N.H., stitchbonded fabric sold by the Milliken & Company of Spartanburg, S.C., or a loop material available from Guilford Mills, Inc., Greensboro, N.C. under the trade designation No. 36549. Another suitable loop material can comprise a pattern un-bonded web as disclosed in U.S. Pat. No. 5,858,515 issued on Jan. 12, 1999 to Stokes et. al. The fact that the dual surface (i.e., two separate surfaces) is required to enable hook and loop style mechanical fastener makes it a costly material, decreases flexibility of mechanical fastening system, and therefore creates limitations for its use.

Mechanical fastening systems have been devised which provide for repeated refastening as well as being lightweight and secure. Hook and loop type mechanical fastening systems, such as Velcro-style fasteners, are well known in the art. Such fastening systems involve two major components, a male component and a female component. The male component typically includes a backing material with a number of protruding hooks that are designed to engage with a number of loops on a complimentary female component. The hooks protruding from the backing material of the male component typically project perpendicularly to the direction of fastener shear force. The hooks typically have a base, a shank, and an engaging means in the form of a hook, cap, or spherical or hemispherical shape. Generally, loop fastening materials will comprise loops, fibers, or the like with the engaging elements of the hook fastening material can become entangled.

When the mechanical fastening system is fastened and shear force acts upon the fastening system, the hooks pull toward the direction of fastener force. As the hooks are pulled which can result in the hooks releasing the loops, the mechanical fastening system may become unfastened as a final result. Furthermore, the fastener force applied to the loops during disengagement may result in damage to the loops, such as loop breakage, fiber pull-out and string-out. Furthermore, the male component often produce red-marking and irritation if brought into contact with a person's skin, such as an infant's skin in contact with a male component of a diaper mechanical fastening system.

There is a need or desire for a male component of a mechanical fastening system that is capable of remaining fastened to a female component under effective levels of shear force while not damaging or distorting the female component.

There is a need or desire for a more universal male component of a mechanical fastening system that is capable of engaging into a wide variety of different potential female components, such as fabrics used in garment manufacturing, e.g. knitted fabrics, woven fabrics, non-woven fabrics, and the like. There also is a need or desire for a male component of a mechanical fastening system that is capable of remaining fastened to an above-specified group of female components under in-use levels of shear force while not damaging or distorting the female component. There is also a need or desire for a male component that is capable to release or disengage from the female component under the effective levels of peel force during disengagement while not damaging or distorting the female component. There is also a need or desire for a male component that can be securely re-attached to the female component after disengagement.

There is also a need or desire for a male component of a mechanical fastening system that reduces or eliminates the occurrence of red-marking and/or irritation if brought into contact with a person's skin.

SUMMARY OF THE INVENTION

The present invention is directed to a male component of a mechanical fastening system such as hook and loop fastener, comprising protrusions wherein at least a portion of the protrusions may be angled toward the direction of fastener shear force acting on the mechanical fastening system in use. The angled protrusions may withstand a higher shear force than conventional perpendicular hooks on the male component without becoming disengaged from the female component, such as loop material, resulting in an advantageously more secure mechanical fastening system. The angled protrusions of the male component may be disengaged from the female component of the mechanical fastening system without causing damage to the above-mentioned female component. The angled protrusions on the male component may reduce skin irritation often caused by perpendicular hooks.

The angled protrusions are non-hook type angled protrusions located on the male component. In some embodiments of the present invention, the entire surface of the male component may be covered with angled protrusions, the surface of the male component may have a combination of perpendicular protrusions and angled protrusions, or the surface of the male component may have a combination of zones covered with angled/perpendicular protrusions and zones with no protrusions. The protrusions, angled and/or perpendicular, on the male component may have similar or different heights.

The angled protrusions may be formed from a mold designed to produce such protrusions, or from a mold specially shaped to produce angled protrusions When the male component is removed from the mold. In some situations, the protrusions may be formed from a mold designed to produce perpendicular protrusions, and then angled in the after-treatment. Alternatively, the angled protrusions may be formed by using two or more polymers side-by-side in a mold, such that the protrusions become angled as the polymers cool due to differential shrinkage of the polymers.

With the foregoing in mind, it is a feature and advantage of the present invention to provide a male component of a mechanical fastening system that may remain fastened to a female component under the in-use levels of shear force without causing noticeable damage or distortion of the female component.

It is another feature and advantage of the present invention to provide a male component of a mechanical fastening system that may be released or disengaged from the female component under effective levels of peel force without causing noticeable damage or distortion of the female component.

It is another feature and advantage of the present invention to provide a male component of a mechanical fastening system that may engage a variety of different materials serving as female components, such as knitted, non-woven, and woven materials.

It is yet another feature and advantage of the present invention to produce a mechanical fastening system that includes the above male component.

It is another feature and advantage of the present invention to provide a male component of a mechanical fastening system that reduces or eliminates the occurrence of red-marking and/or irritation if brought into contact with a person's skin.

In another aspect, the invention resides in an elongated absorbent pad having two ends, two side edges, an absorbent surface for contacting the body of a user and a backsheet with a back surface for contacting the clothing of the user, said back surface having one or more protrusion islands positioned within each end of the pad and one or more protrusion islands centrally positioned inside each of the side edges of the pad for attaching the absorbent pad to the clothing of the user, wherein the protrusion islands contain a plurality of outwardly extending first protrusions and a plurality of outwardly extending second protrusions, said protrusions having a height from about 0.003 centimeters to about 0.9 centimeters and a Flexural Modulus from about 331 MPa to about 2,758 MPa, wherein the first protrusions extend at an angle from about 5 degrees to about 85 degrees relative to the back surface and the second protrusions extend at an angle from about 95 degrees to about 175 degrees relative to the back surface.

BRIEF DESCRIPTION OF THE DRAWINGS

FIG. 6a-b is a side view of an angled protrusion on a male component of a mechanical fastening system of the present invention.

FIGS. 7a-7d are side views of angled protrusions on male components of mechanical fastening systems of the present invention.

FIGS. 8a-8f are cross-sectional views of protrusions of mechanical fastening systems of the present invention.

DEFINITIONS

Figure 1:
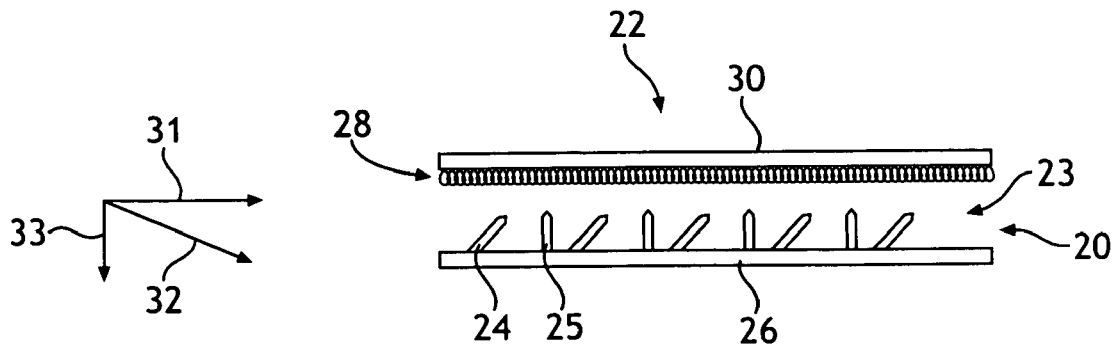
FIG. 1 is a side view of a male component and a female component of a mechanical fastening system of the present invention prior to engagement with one another.

Within the context of this specification, each term or phrase below will include the following meaning or meanings.

"Angled Protrusion" refers to a protrusion comprising a base and a shank that extends from the backing of a male component of a mechanical fastening system, and is non-perpendicular to a male component backing.

"Comprises", "Comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Accordingly, such terms are intended to be synonymous with the words "has", "have", "having", "includes", "including" and any derivatives of these words.

"Direction of Fastener Force" refers to a force exerted by the male component on the female component while the components are engaged (e.g. while the article embodying the fastener is being worn). The fastener force is a vector force having a shear force component and a normal force component.

"Engaging Portion" refers to a part of a fastening component that is suitably shaped to enable the fastening component to engage or secure itself to a complementary fastening component. Examples of engaging portions include J-shaped hooks, and flat-topped hook portions atop protrusions having a diameter narrower than the flat top.

"Extensible Material" refers to a material that can a provide a substantially. permanent deformation of at least about 10 percent, desirably at least about 15 percent, particularly at least about 17 percent, more desirably at least about 20 percent, even more desirably at least about 25 percent, and yet even more desirably at least about 30 percent when subjected to a tensile force of 100 gmf per inch (per 2.54 cm) of width according to the Material Elongation and Deformation Tensile Test set forth herein. In general, the Material Elongation and, Deformation Tensile Test is conducted similar to ASTM Standard Test Method D882 (Tensile Method for Tensile Properties of Thin Plastic Sheeting) dated December 1995. The initial separation of the jaws of the tensile tester is 3 inches (76.2 mm) at a tensile force of about 1 gram force per inch of width of the test sample, and the moving jaw is moved at a constant rate of 127 mm/min. The moving jaw is stopped at an extension where the tensile force equals 100 grams force per inch of width of the test sample, held at that extension for a period of 2 minutes, and then returned back to its initial tensile force of about 1 gram force per inch of width of the test sample at a rate of 127 mm/min.

"Knitted Fabric" refers to a cloth constructed by interlocking a series of loops of one or more yarns by hand or by machine, by a knitting process. Three main classes of knit fabrics are circular knit, flat knit and warp knit. Examples of the last type of knit include *Tricot, Milanese* and Raschel knit.

"Knitting Process" refers to a method of constructing fabric by interlocking series of loops of one or more yarns.

"Meltblown Fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

As used herein, the term "Non-elastic", what is meant is that the sheet layers are made from polymers that are generally considered to be inelastic. In other words, use of such inelastic polymers to form the sheet layers would result in sheet layers that are not elastic. As used herein, the term "Elastic" means any material which, upon application of a biasing force, is stretchable, that is, elongatable, at least about 60 percent (i.e., to a stretched, biased length which is at least about 160 percent of its relaxed unbiased length), and which will immediately recover at least 55 percent of its elongation upon release of the stretching, elongating force.

As used herein, the term "Non-woven" means a fabric or web having a structure of individual fibers or threads which are interlaid, but not in a regular or identifiable manner as in a knitted textile or woven textile fabric. Non-woven fabrics or webs have been formed from many processes such as, for example, melt-blowing processes, spunbonding processes, air laying processes, and bonded carded web processes. The basis weight of non-woven fabrics is usually expressed in ounces of material per square yard (osy) or grams per square meter (gsm) and the fiber diameters useful are usually expressed in microns. (Note that to convert from osy to gsm, multiply osy by 33.91.)

"Perpendicular Direction" or "Perpendicular Force Direction" refers to a direction normal (90 degrees) to a backing material or other reference surface. The perpendicular direction is perpendicular to the shear direction, defined below.

"Perpendicular Force", or "peel force" refers to forces that tend to produce an opposite pulling motion in a perpendicular direction between two bodies' planes.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Releasably Attached," "Releasably Engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the garment item.

"Resilient" refers to a material that is flexible, compressible and reformable.

"Shear Force" refers to forces that tend to produce an opposite but parallel sliding motion between two bodies' planes.

"Shear Direction" or "Shear Force Direction" refers to a direction parallel to a backing material or other reference surface undergoing shear force.

As used herein, the term "Spunbonded Fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and of-ten have average diameters larger than about 7 microns, more particularly, between about 10 and 30 microns.

"Thermoplastic" describes a material that softens when exposed to heat and which substantially returns to a nonsoftened condition when cooled to room temperature.

"Water-permeable Porous Films" refers to films rendered porous by puncturing or aperturing, and to films rendered porous by mixing polymer with filler, forming a film from the mixture, and stretching the film.

"Woven Fabric" refers to fabric that is formed by a weaving process of interlacing of at least two sets of yarns. Woven fabric may be composed of two sets of yarns, warp and filling. Woven fabrics may be composed of three sets of yarn to provide a triaxial weave. Two dimensional woven fabrics may be composed of two or more warps and fillings in a fabric, depending on the complexity of the construction of the fabric. The manner in which the two sets of yarn are interlaced determines the weave. The weaving process may include one or more basic weaves, such as plain, twill, and satin.

"Yarn" refers to a continuous strand of textile fibers, filaments, or material in a form suitable for knitting, weaving, or otherwise intertwining to form a textile fabric. Yarn may be provided in the following forms: (1) a number of fibers twisted together (spun yarn); (2) a number of filaments laid together without twisting (a zero-twist yarn); (3) a number of filaments laid together with a degree of twist; (4) a single filament with or without twist (a monofilament); or, (5) a narrow strip of material, including but not limited to, paper, plastic film, or metal foil, or metal foil, with or without twist, intended for use in a textile construction.

These terms may be defined with additional language in the remaining portions of the specification.

DETAILED DESCRIPTION OF THE INVENTION

The present invention is directed to a mechanical fastening system that includes a male component and a female component. In the present invention, a male component of a mechanical fastening system, such as hook and loop fastener system, may be fastened to a variety of different materials serving as a female component and may remain securely fastened to the female component under effective levels of shear force. The materials may include fabrics, such as: (i) woven textile fabrics; (2) knitted textile fabrics; and, (3) non-woven materials. For the purposes of the present invention, the term "fabrics" is used to refer to woven, knitted, and non-woven webs.

The present invention may also be directed to a male component of a mechanical fastening system that may be easily released or disengaged from the female component under the effective levels of peel force without causing noticeable damage or distortion to the loop material, and may be securely re-attached if needed after several engagement—disengagement cycles. The male component includes protrusions wherein at least a portion of the protrusions may extend from a backing material at an angle toward the direction of fastener shear force. The geometry of the male component can also reduce or eliminate the occurrence of red-marking and/or irritation if brought into contact with a person's skin during use of the disposable absorbent article.

The male component of mechanical fastening system of the present invention may be utilized when a material comprising the male component would be attached in a refastenable manner to a garment or an undergarment material. Examples of applications of this particular type of mechanical fastener include, but are not limited to using a male component of the present invention to:

(1) refastenably attach a shoulder strap or another part of an undergarment, e.g. brassiere, to the undersurface of an overlying garment or used to attach any piece of one garment, e.g. an undergarment such as panties or breast caps, to overlying garments, thereby preventing shifting during use;

(2) secure a disposable absorbent article, such as an adult incontinence pad or a feminine care pad, to the wearer's undergarment;

(3) adjust the waistline of a garment or an undergarment by either tightening or un-tightening waistline band or waistline flaps, and re-attaching them to the garment and/or to themselves at a desirable waistline width or used to close and/or adjust width of collars, sleeve cuffs, or leg cuffs of garments;

(4) attach various functional and fashionable additions to a garment article, e.g. additional pockets, re-attachable sleeves, re-attachable hoods, or seasonal decorative appliqués, such as pumpkin or autumn leaf shapes for Thanksgiving, or used to create a wide variety of fashionable, decorative designs from the same basic piece of garment;

(5) make creativity toys for kids, e.g. animal and alphabet shapes that can be attached to a fabric covered board;

(6) refastenably attach name tags and visitors badges to the garments;

It should be appreciated by those skilled in the art that these examples are given for purposes of illustration and are not to be construed as limiting the scope of the application of the present invention.

This male component is particularly suitable for use in mechanical fastening systems on disposable absorbent articles in which the fastener force has a significant shear force component during use. The term "disposable absorbent garments" is intended to refer to any disposable garment intended to absorb discharged body fluids. Examples of disposable absorbent garments include diapers, adult incontinence products, training pants, feminine napkins, wound dressings, and the like. For ease of understanding, much of the following description will be made in terms of the use of the mechanical fastening systems of the present invention on disposable absorbent products, such as, feminine-care products and disposable diapers. Nonetheless, it is to be understood that the mechanical fastening systems of the present invention are equally suited for use on any other disposable absorbent products or durable products.

As shown in FIG. 1, a male component 20 and a female component 22 may be brought together to be releasably attached, or releasably engaged, to one another. The male component 20 may have a number of individual stems or protrusions 23 extending from a resilient backing material 26. Similarly, the female component 22 may have a number of individual loops 28 protruding generally perpendicularly from a resilient loop backing material 30. It is understood, as used herein, the female component 22 may comprise a part or a component of a garment article; alternatively, the female component 22 may comprise a part or a component of the disposable absorbent article 10 or a knitted textile fabric, woven textile fabric, and/or non-woven web that the disposable absorbent article 10 comes in contact with during use. The individual protrusions 23 of the male component 20 and the loops 28, such as individual fibers or bungles of fibers, of the female component 22, when brought into contact with one another, engage or interlock with one another, with the protrusions 23 of the male component 20 latching onto the loops 28 of the female component 22, until forcibly separated, thereby pulling the protrusions 23 of the male component 20 out of the loops 28 of the female component 22. The male and/or female components 20 and 22, respectively, may be attached to the disposable absorbent article 10 or to a peripheral portion thereof, such as wing structures.

In some embodiments of the present invention, the individual loops 28 of the female component 22 may be needled, stitched or otherwise projected through the loop backing material 30. The loop backing material 30, or alternatively, the female component 22 may suitably be made from a non-woven material. In another embodiment of the present invention, the female component 22 may suitably be made from a fibrous non-woven web such as a spunbond non-woven web, or a staple fiber carded web. An example of a suitable non-woven web is disclosed in U.S. Pat. No. 5,858,515 to Stokes, et. al, and is hereby incorporated by reference. Alternatively, the individual loops 28 may be made of yarn or tow. Once the loops 28 have been formed, fibers forming the loops 28 may be anchored in place by bonding the fibers to the loop backing material 30 with heat and/or adhesives or any other suitable means. Such suitable female components 22 are available from Velcro, USA, of Manchester, N.H. Alternatively, the female component 22 may be a woven or knitted textile fabric, such as one of the fabrics conventionally used for garment or underwear manufacturing. It is to be understood that the individual loops 28 may not protrude from the surface of the female component 22 but may be an integral part of a fabric, as in typical knitted textile fabric, woven textile fabric, or non-woven webs.

Figure 2:
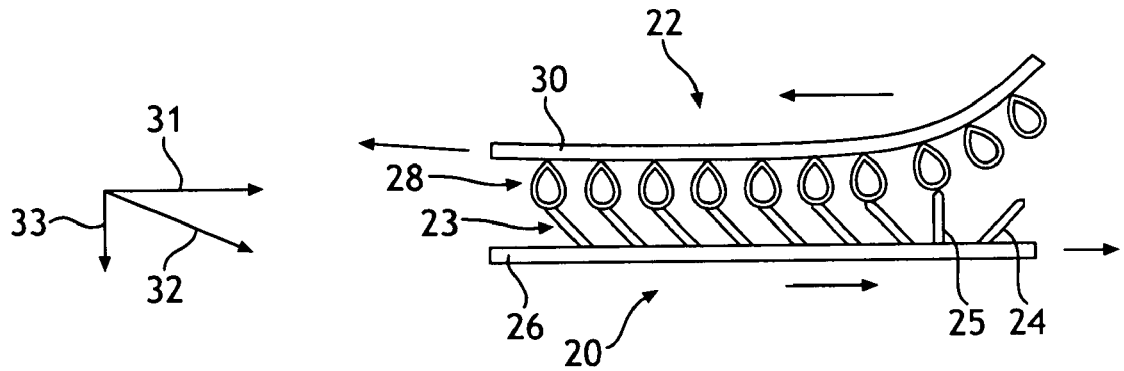
FIG. 2 is a side view of a male component of a mechanical fastening system of the present invention shown in partial engagement with a female component.
Figure 5:
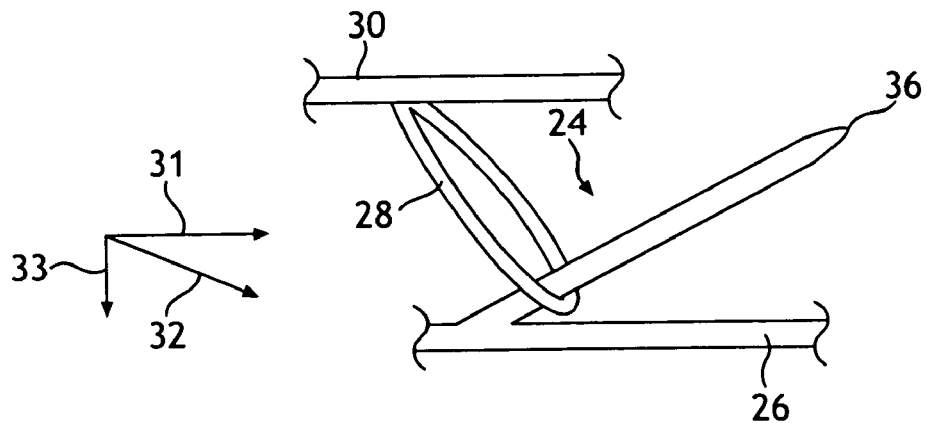
FIG. 5 is a side view of an angled protrusion on a male component of a mechanical fastening system of the present invention engaged with a female component.

At least some of the individual angled protrusions 24 of the male component 20 of the present invention may be angled, at least in part, toward the direction of fastener shear force. As used herein, the term "direction of fastener shear force" refers to a shear component of a direction, i.e., the direction of fastener force, which a male component 20 applies to a mating female component 22 when the male and female components 20 and 22, respectively, are engaged and under tension. FIG. 2 shows the male component 20 and the female component 22 of FIG. 1 in an engaged position under tension, wherein part of the male and female components 20 and 22 are undergoing disengagement. The direction of fastener force is indicated by arrow 32 in FIGS. 1 and 2. The direction of fastener shear force is indicated by arrow 31 in FIGS. 1 and 2. The direction of a perpendicular peel force component of the fastener force is indicated by arrow 33 in FIGS. 1 and 2. As shown in FIG. 1 and 2, as typically observed during use, the shear component of the force acting on the mechanical fastening system may be much higher than the peel component of the force acting on the mechanical fastening system. The fastener shear force is in direct opposition to shear force exerted by the female component 22 against the male component 20. If the angled protrusions 24 of the male components 20 are relatively flexible, the loops 28 of the female component 22 may bend the angled protrusions 24 in a direction opposite the direction of their original tilt, as shown in FIG. 2. Alternatively, the angled protrusions 24 may be relatively stiff, thereby latching the loop 28 between the protrusion 24 and the backing material 26, as shown in FIG. 5, and providing for a very secure attachment.

Figure 2A:
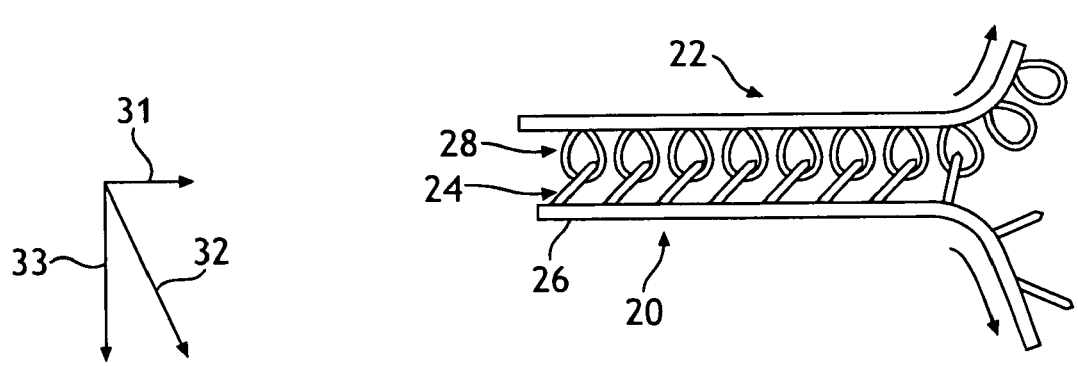
FIG. 2a is a side view of a male component of a mechanical fastening systems of the present invention shown in partial disengagement from a female component by the application of a peel force.

When it is necessary to disengage or unfasten a mechanical fastening system, an unfastening force having a higher perpendicular peel force component than parallel shear force component may be applied to the mechanical fastening system (see FIG. 2a). The geometry of the angled protrusions 24 and properties of the materials making up the angled protrusions 24 may ensure that the loop 28 are not pulled out from or otherwise damaged during the release stage. The angled protrusions 24 may require only slight deformation, such as bending, to be released, which can be achieved by application of the low-to-moderate levels of perpendicular peel force. Thus, much lower values of forces may be applied to the female component 22 during the separation stage in case of angled protrusions 24 than in case of a conventional hook material-based male component. In order to further reduce or prevent damage to the female component 22 during the release stage, only the materials with the appropriate flexibility characteristics may be chosen for manufacturing of angled protrusions 24, i.e. materials with Flexural Modulus of between about 331 MPa to about 2,758 MPa (see more detailed discussion of the flexibility of protrusions below), alternatively, about 344.7 MPa to about 2,413 MPa, or alternatively about 413.7 MPa to about 2,344 MPa. The lower limit of the Flexural Modulus may be independently about 331 MPa, about 344.7 MPa, about 379.2 MPa, or about 413.7 MPa. The upper limit of the Flexural Modulus may be independently about 2,344 MPa, about 2,413 MPa, or about 2,758 MPa.

For some embodiments of the present invention, the materials may have a Flexural Modulus of between about 331 MPa to about 586 MPa, alternatively, about 338 MPa to about 572 MPa, or alternatively, about 345 MPa to about 552 MPa. The lower limits of the Flexural Modulus may be independently about 331 MPa, about 338 MPa, or about 345 MPa. The upper limit of the Flexural Modulus may be independently about 552 MPa, about 572 MPa, or about 586 MPa.

In some embodiments of the present invention, the materials may have a Flexural Modulus of between about 965 MPa to about 1,379 MPa, alternatively, about 1,034 MPa to about 1,310 MPa, or alternatively, about 1,103 MPa to about 1,241 MPa. The lower limits of the Flexural Modulus may be independently about 965 MPa, about 1,034 MPa, or about 1,103 MPa. The upper limit of the Flexural Modulus may be independently about 1,241 MPa, about 1,310 MPa, or about 1,379 MPa.

In other embodiments of the present invention, the materials may have a Flexural Modulus of between about 1,724 MPa to about 2,344 MPa, alternatively, about 1,793 MPa to about 2,275 MPa, or alternatively, about 1,862 MPa to about 2,206 MPa. The lower limits of the Flexural Modulus may be independently about 1,724 MPa, about 1,793 MPa, or about 1,862 MPa. The upper limit of the Flexural Modulus may be independently about 2,206 MPa, about 2,275 MPa, or about 2,344 MPa.

Figure 3:
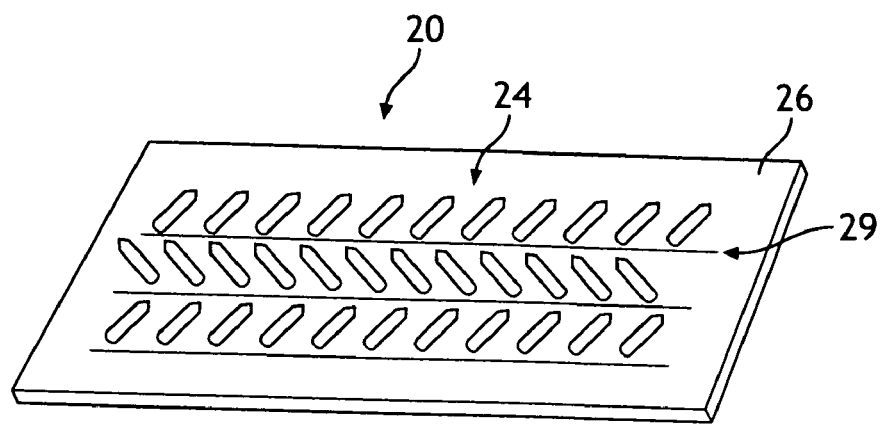
FIG. 3 is a perspective view of a male component of a mechanical fastening system of the present invention.

The angled projections 24 may be able to handle a greater amount of fastener shear force 31 exerted by the female component 22 than typical perpendicular projections 25 because the female component 22 must overcome a greater amount of fastener shear force 31 when the angled projections 24 are angled toward the direction of fastener shear force 31. Male components 20 having angled projections 24 thereby may result in a more secure fastening system. To address opposite directions of fastener shear force 31 that may be subjected to the mechanical fastening system during use and separation, depending on the directions in which the female component 22 moves during use and during separation from the male component 20, angled projections 24 are suitably located in opposite directions, as illustrated in FIG. 3. Furthermore, the angled projections 24 and perpendicular projections 25 reduce the number of sharp ends poking a wearer by pointing sharp ends away from the wearer, and may thus reduce skin irritation often caused by conventional hook structures.

Figure 9:
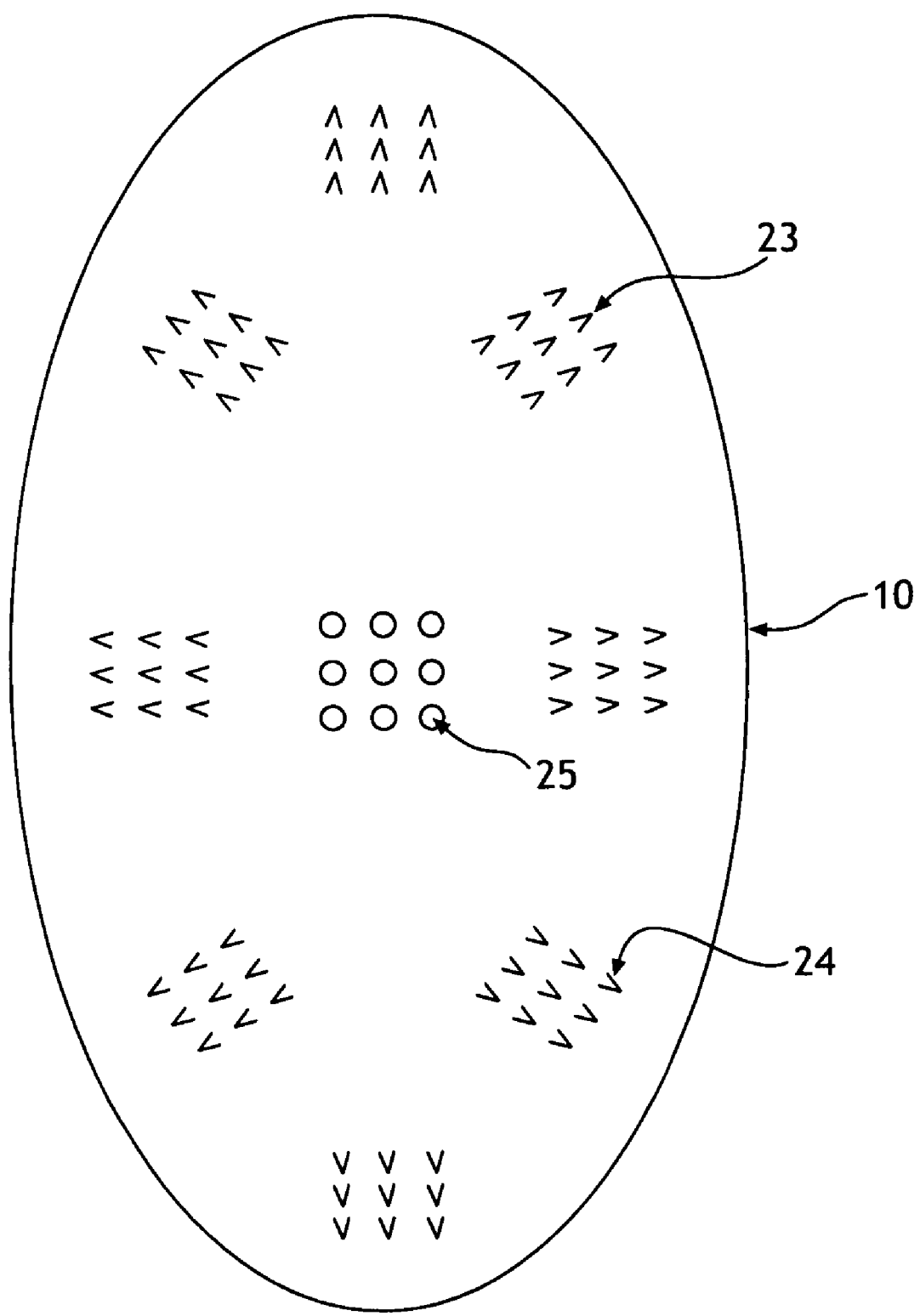
FIG. 9 is a plan view of a garment-facing side of a disposable absorbent article incorporating a male component of a mechanical fastening system of the present invention.
Figure 11:
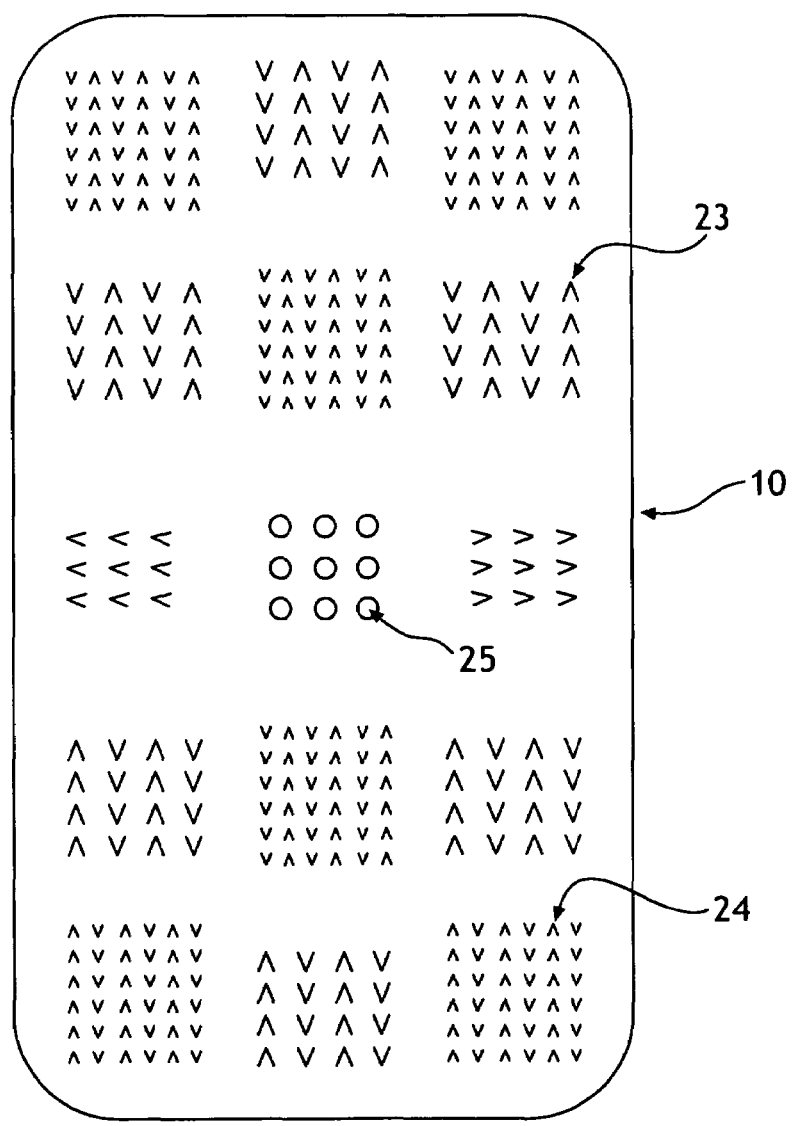
FIG. 11 is a plan view of a garment-facing side of an absorbent article consisting of multiple groups of protrusions.

All of the individual protrusions 23 of the male component 20 may be angled protrusions 24 which are angled toward the direction of fastener shear force 32 or, alternatively, some of the individual protrusions 23 may be angled protrusions 24, angled toward the direction of fastener force 32 and some of the individual protrusions 23 may be perpendicular protrusions 25, roughly perpendicular to the backing material 26 (and roughly perpendicular to the direction of fastener shear force 31). A combination of angled protrusions 24 and perpendicular protrusions 25 is shown in FIG. 1 and FIGS. 9 and 11. Individual angled protrusions 24 that are angled non-perpendicular to the backing material 26 are suitably at an angle ($\alpha$) of about 5 degrees to about 85 degrees with respect to the backing material 26 (and the direction of fastener shear force 31), more suitably at an angle ($\alpha$) of about 15 degrees to about 80 degrees, more suitably at an angle ($\alpha$) of about 15 degrees to about 75 degrees, more suitably at an angle ($\alpha$) of about 20 degrees to about 75 degrees, more suitably at an angle ($\alpha$) of about 30 degrees to about 75 degrees, most suitably at an angle ($\alpha$) of about 35 degrees to about 70 degrees (See FIGS. 7a-7d). The lower limit of the angle ($\alpha$) of the individual protrusions 23 may be independently about 5 degrees, about 15 degrees, about 20 degrees, about 30 degrees, or about 35 degrees. The upper limit of the angle ($\alpha$) of the individual protrusions 23 may be independently about 85 degrees, about 80 degrees, about 75 degrees, or about 70 degrees.

Individual protrusions 25 that are roughly perpendicular to the backing material 26 and direction of fastener shear force 31, are suitably at an angle ($\alpha$) of about 70 degrees to about 110 degrees with respect to the backing material 26, more suitably at an angle ($\alpha$) of about 80 degrees to about 100 degrees, and most suitably at an angle ($\alpha$) of about 85 degrees to about 95 degrees. The lower limit of the angle ($\alpha$) of the individual protrusions 25 may be independently about 70 degrees, about 80 degrees, or about 85 degrees. The upper limit of the angle ($\alpha$) of the individual protrusions 25 may be independently about 110 degrees, about 100 degrees, or about 95 degrees.

The protrusions 23 of the male component 20 penetrate the surface of or otherwise interact with the female component 22. The protrusions 23 of the male component 20 may comprise a variety of sizes and shapes. FIGS. 7a to 7d show four side views of different shapes that the protrusions 23 may assume. The protrusions 23 may terminate in tapered ends (see FIG. 7b) or may comprise conical or pyramidal shapes (see FIG. 7c). In other embodiments the protrusions 23 may comprise the shape of a truncated cone or a truncated pyramid (see FIG. 7d). FIGS. 8a to 8g show seven additional cross-sectional views of shapes that the protrusions 23 may also assume.

It may be desirable that the cross-sectional dimensions of the protrusions 23 of the male components 20 of the present invention are comparable or smaller than the size of the void spaces between the fibers in the female component 22. The cross-sectional dimensions of the protrusions 23 may range from about 90 to about 500 μm, more specifically from about 130 to about 440 μm, and most specifically from about 160 to about 400 μm. The lower limit of the cross-sectional dimension of the protrusions 23 may be independently about 90 μm, about 130 μm, or about 160 μm. The upper limit of the cross-sectional dimension of the protrusions 23 may be independently about 500 μm, about 440 μm, or about 400 μm. The cross-sectional dimensions of the protrusions 23 may be variable along the length of protrusion as shown in FIGS. 6b, and 7b to 7d. Such variability in the cross-sectional dimensions of the protrusions 23 may allow the protrusions 23 to penetrate and engage a variety of female components 22 having void spaces of different sizes or variable sizes. In an alternative embodiment, male component 20 may include two or more groups of protrusions 23, each group of protrusions 23 being characterized by specific cross-sectional dimensions (see FIGS. 9 and 11), thereby enabling the male component 20 to attach to a variety of female components 22.

Figure 4:
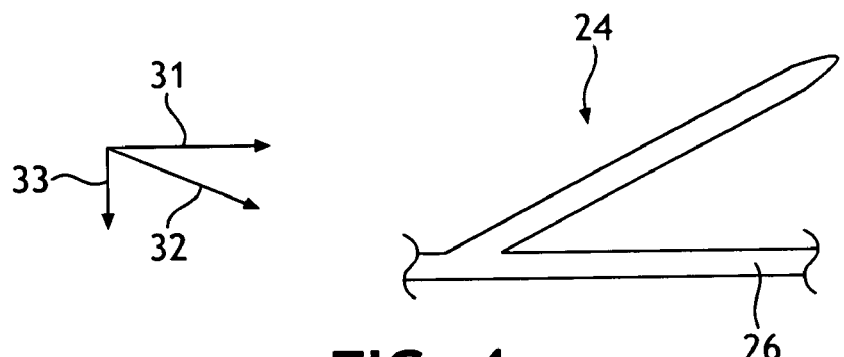
FIG. 4 is a side view of an angled protrusion on a male component of a mechanical fastening system of the present invention.

The angled projections 24 may be more angled along a small portion, such as at one end 27, as shown in FIG. 6, or along a substantial length of the angled projection 24, as shown in FIGS. 4 and 5. The term "substantial length," as used herein, refers to the full length of the angled projection 24.

In accordance with some embodiments, the male components 20 of the present invention may generally have between about 16 and about 930 protrusions 23 per square centimeter, more specifically between about 124 and about 470 protrusions 23 per square centimeter, and most specifically between about 155 and about 310 protrusions 23 per square centimeter. In other embodiments of the present invention, the male components 20 may generally have between about 250 to about 800 protrusions 23 per square centimeter, more specifically between about 350 to about 700 protrusions 23 per square centimeter, and most specifically between about 400 to about 600 protrusions 23 per square centimeter. In other embodiments of the present invention, the protrusions 23 of the male components 20 may form a discontinuous pattern, such as stripes and isolated islands, wherein the number of protrusions 23 may range from about 5 protrusions 23 per square centimeter or greater.

The heights h of the protrusions 23 of the male components 20 of the present invention may range from about $3 \times 10^{-3}$ cm to about 0.9 cm, more specifically from about $2.4 \times 10^{-2}$ cm to about $5.5 \times 10^{-2}$ cm, and most specifically from about $2.8 \times 10^{-2}$ cm to about $5 \times 10^{-2}$ cm. The lower limit of the height of the protrusions 23 may be independently about $3 \times 10^{-3}$ cm, about $2.4 \times 10^{-2}$ cm, or about $2.8 \times 10^{-2}$ cm. The upper limit of the height of the protrusions 23 may be independently about 0.9 cm, about $5.5 \times 10^{-2}$ cm, or about $5 \times 10^{-2}$ cm. (See FIGS. 7a to 7d). The height of the protrusions 23 should provide effective engagement of the protrusions 23 of the male component 20 and the female component 22.

The protrusions 23 may be formed by injection molding, cavity molding, profile extrusion, or any other fabricating process known in the art. For example, the protrusions 23 may be suitably molded or extruded using a continuous molding process, in which a plastic resin strip base is molded with integral fastener elements in the form of protrusions extending from one surface. Such molding may be performed in a high pressure nip, such as between two counter-rotating rollers or against a single roller that defines miniature cavities in its peripheral surface, the cavities may be shaped in such a way that the cavities would be suited for molding any shape of the protrusions 23, including the shapes shown in FIGS. 6 and 7a-d. One process is described in the U.S. Pat. No. 4,794,028, issued on Dec. 27, 1988 to Fisher, and incorporated herein by reference to the extent it is consistent herewith. Alternatively, a method of in situ lamination of protrusions 23 to the backing material 26 may be used, as disclosed in U.S. Pat. No. 5,260,015, issued on Nov. 9, 1993 to Kennedy et. al., and incorporated herein by reference to the extent it is consistent herewith. The materials for making the protrusions 23 may be selected from a group of thermoplastic polymers such as polyamides, polyesters, poly(vinyl acetate), PVC, polyolefins (e.g. polyethylene, polypropylene, polybutene, ethylene copolymers, propylene copolymers, or butene copolymers), a thermoplastic elastomer, or another suitable material and mixtures thereof.

The Flexural Modulus of the material from which the protrusions 23 may be suitably molded or extruded should be in the range from about 331 MPa to about 2,758 MPa. As used herein, the term "Flexural Modulus" is used as an equivalent of a term "Modulus of Elasticity in Bending" and refers to a characteristic of the flexural properties of plastics determined according to ASTM D 790-99 "Standard Test Methods for Flexural Properties of Unreinforced and Reinforced Plastics and Electrical Insulating Materials". Protrusions 23 having such flexural modulus provides for acceptable engagement with the female component 22 while maintaining flexibility to allow disengagement from the female component 22 without causing significant damage. Other parameters of the protrusions 23 that may affect the flexibility, engagement and disengagement characteristics of the protrusions 23 include, but are not limited to: (a) the length/height of a protrusion 23; (b) the angle α between the protrusion 23 and the backing material 26; and, (c) the cross-sectional area (or shape) of the protrusions 23. As the cross-sectional area of protrusions 23 is increased (e.g., thicker stems), the flexibility of the protrusions 23 may decrease. To compensate for reduced flexibility of the protrusions 23, selection of materials having lower Flexural Modulus may be made. Likewise, when the angle α between the protrusions 23 and the backing material 26 is decreased, or when the length of protrusions 23 is increased, the selection of materials having an appropriate Flexural Modulus may be 5 needed to provide protrusions 23 of desired flexibility. For example, materials having a lower Flexural Modulus to increase the flexibility of the protrusions 23, thereby and thus avoid significant separation forces acting on the female component 22 during disengagement.

The protrusions 23 may be comprised of more than one material. In some embodiments of the present invention, the protrusions 23 may be made of one polymer or material that may provide a desired trait or characteristic and be coated with another polymer or material that may provide an additional trait or characteristic. For example, the protrusion 23 may be comprised of polypropylene which may provide a mechanical strength. Such a protrusion 23 may then be coated with a pliable or elastomeric material, such as a silicone rubber, ethyl-vinyl-acetate (EVA), homo- and co-polymers of isoprene, homo- and co-polymers of butadiene, and the like, to provide a softer¡ more skin-friendly surface and a surface with a higher coefficient of friction, such as materials with a coefficient of friction higher than 1.

Figure 10:
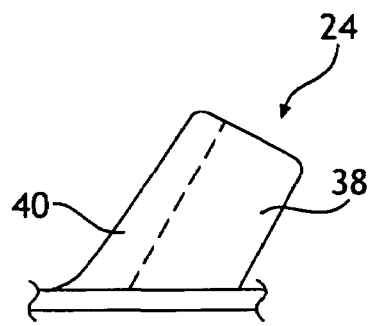
FIG. 10 is a side view of an angled protrusion comprised of two different materials on a male component of a mechanical fastening system of the present invention.

Alternatively, the method of manufacture may be modified by using at least two different polymers 38 and 40 aligned side-by-side along a length of the protrusion mold. When the polymers 38 and 40 are heated, all of the polymers 38 and 40 should be heat softened. In some embodiments of the present invention, the polymers 38 and 40 may be chosen such that one polymer 38 shrinks more than the other polymer 40 or other polymers during the cooling process. Thus, when the polymers 38 and 40 cool, the polymer 38 that shrinks more lowers the protrusion 24 toward the backing material 26 while the polymer 40 that shrinks less forms a surface away from the backing material 26, as shown in FIG. 10.

The backing material 26 may be made of any of the materials that comprise the protrusions 23 or any other suitable materials. The backing material 26 may be made of the same or a different material than the protrusions 23 of the male component 20. The backing material 26 may generally have a thickness in a range of between about 0.1 millimeter (mm) and about 5 mm, suitably in a range of between about 0.6 mm and 2 mm, resulting in a total basis weight of the male component 20 in a range of from about 20 grams per square meter to about 200 grams per square meter. In various embodiments of the present invention, the backing material 26 may comprise a film, a paper, a knit fabric, woven, needle punched non-woven, spunbond, point-unbonded non-woven material (PUB), neck bonded laminate (NBL), spunbond/meltblown/spunbond multi-layer laminate, air laid non-woven, air-formed non-woven, and the like.

The protrusions 23 of the male component 20 of the present invention may be spatially arranged in rows with spacers 29 between the rows, as shown in FIG. 3. These spacers 29 may be in the form of bumps, ridges, depressions, or any other suitable distortion made in or added to the backing material 26. These spacers 29 may improve the overall flexibility of the backing material 26 by providing areas of lower density among the individual protrusions 23 where the backing material 26 may easily bend to conform to a wearer's body as the body moves. Furthermore, the spacers 29 may also improve the flexibility of individual protrusions 23 by providing room for the individual protrusions 23 to bend in response to applied pressure. Alternatively, the rows of protrusions 23 may be separated by a flat surface. Also, as mentioned, the protrusions 23 may be suitably arranged such that a plurality of the protrusions 23 face one direction and a plurality of the protrusions 23 may face an opposite direction or a different direction in order to compensate for directions of fastener forces in opposite/different directions. See FIGS. 9 to 10 and FIGS. 14a to 14b for examples of possible orientations of angled protrusions. In other embodiments of the present invention, the angled protrusions 24 of the male component 20 may be randomly oriented in different directions. The orientations may be in the machine direction (MD) and/or cross-machine direction (CD) and any orientation therebetween.

Figure 17:
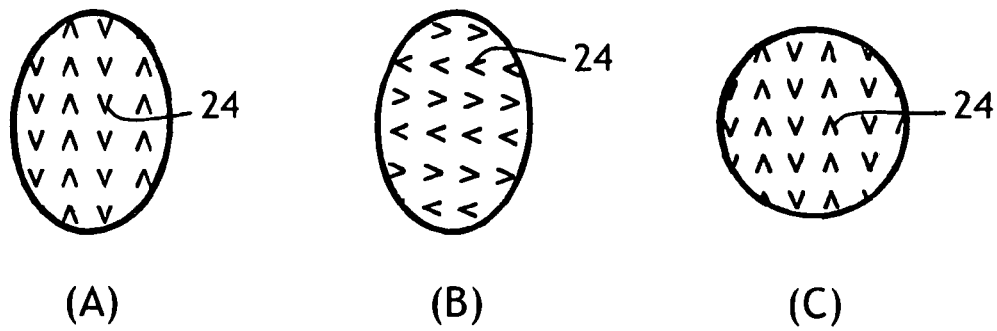
FIG. 17 is a schematic illustration of several representative groups of protrusions or "protrusion islands" which can be used in a multitude of combinations to provide the desired attachment properties in accordance with this invention.

FIG. 17 schematically illustrates three particularly suitable embodiments of protrusion islands (A, B and C). The protrusions 24 consist of a plurality of first protrusions and a plurality of second protrusions, each of which are arranged within each island in alternating rows, meaning that the first protrusions of one row point in one direction and the second protrusions of the adjacent row point in the opposite direction. The direction of the protrusions (indicated by the pointed end of the "V"s) in adjacent alternating rows is further illustrated in FIG. 3. It is believed that having approximately half of the protrusions within a protrusion island pointing in one direction and having the remaining protrusions point in the opposite direction is advantageous because it more effectively engages the weave structure of the user's clothing, particularly undergarments. It also provides for attachment forces in two directions, which enables the pad to remain attached if movement of the pad might cause detachment in one direction. A convenient means of arranging the first and second protrusions within a protrusion island is to provide directionally alternating rows of protrusions as shown. However, it is also suitable to alternate between one or more adjacent rows of first protrusions and one or more adjacent rows of second protrusions (such as -A-B-B-A-B- or -A-A-A-B-B-B- or -A-A-B-B-AA- and the like, where "A" represents a row of first protrusions and "B" represents a row of second protrusions oriented in the opposite direction) as long as there are substantial numbers of protrusions oriented in opposite directions within a protrusion island. The optimum arrangement will depend on the weave structure of the undergarment which provides the openings for the protrusions to fill and thereby engage the fabric. In addition, it is also suitable to provide a row of protrusions with first and second protrusions so that a single row of protrusions has protrusions oriented in opposite directions. For example, the protrusions in such rows can simply alternate between first protrusions and oppositely directed second protrusions, or there may be two first protrusions followed by two second protrusions, or any combination desired. Again, the effectiveness of these various combinations will depend on the weave pattern of the undergarment.

As illustrated in FIG. 17, embodiment "A" is an oval protrusion island in which the directional orientations of the protrusions are aligned with the major axis of the oval. Embodiment "B" is an oval protrusion island in which the directional orientations of the protrusions are aligned with the minor axis of the oval. Embodiment "C" is a circular protrusion in which there is no directional alignment since the circle has no major or minor axis. However, the shape of the protrusion islands can be any shape, such as oval, circular, square, rectangular, hexagonal, etc. or irregular.

It will be appreciated that the size, spacing and number of protrusion islands in any particular absorbent pad will depend on a variety of factors, including the level of attachment desired, the size of the pad, the length of the individual protrusions, the angles of the individual protrusions, the density of the individual protrusions, the flexibility of the individual protrusions and the like. Nevertheless, in general, it is believed that the size (area) of the protrusion islands can be from about 5 to about 100 square millimeters, more specifically from about 10 to about 50 square millimeters, and still more specifically from about 15 to about 40 square millimeters. A-particularly suitable size is about 25 square millimeters.

Figures 18, 19, 20:
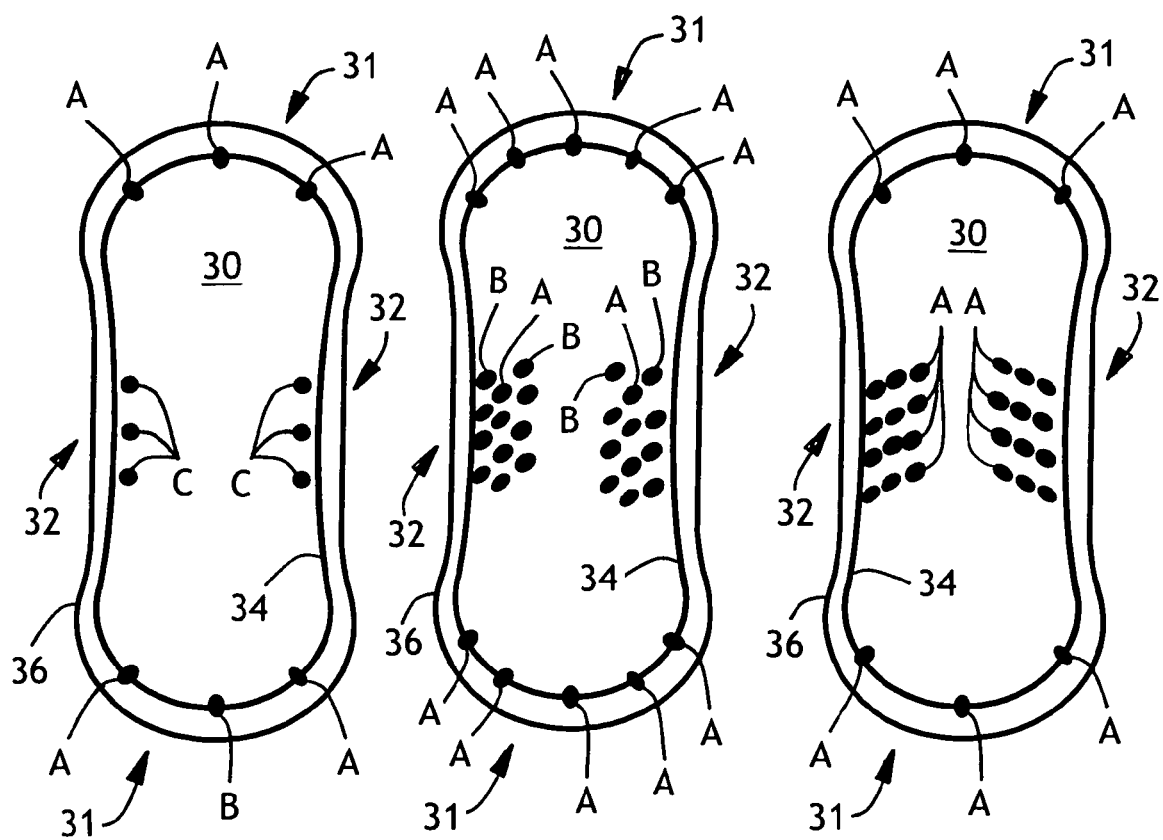
FIG. 18 is a schematic plan view of the clothing-contacting surface of an absorbent pad, such as a feminine pad, in accordance with this invention and similar to FIGS. 9 and 11, illustrating the strategic placement of the protrusion islands within each end of the pad and centrally positioned inside each of the side edges of the pad.
FIG. 19 is a schematic plan view of an absorbent pad in accordance with this invention similar to that of FIG. 18, but showing an embodiment with more protrusion islands, especially in the region of the central side edges.
FIG. 20 is a schematic plan view of another absorbent pad embodiment in accordance with this invention similar to those of FIGS. 18 and 19, but showing the protrusion islands in the central side edge regions being arranged in diagonal parallel rows.

FIG. 18 schematically illustrates an elongated absorbent pad of this invention in which the protrusion islands (represented by solid dots or ovals in this Figure and in FIGS. 19 and 20) are strategically arranged on the back surface 30 of the pad. For reference, also shown are the ends 31 of the pad, the central sides 32 of the pad, the absorbent core edge 34 of the pad and the side edge 36 of the pad. The edge 34 and edge 36 extend around the periphery of the pad, including the sides and ends of the pad. The protrusion islands, which are designated as either A, B or C, correlate with the protrusion islands designated as A, B or C in FIG. 17. The protrusions positioned near the ends of the pad prevent the pad from flipping over/under when the undergarment is pulled up and down when the user is changing clothes or using the bathroom. At the same time, the protrusion islands centrally positioned inside each of the side edges of the pad minimize center bunching of the pad during wear.

In general, it is advantageous to provide each pad with two or more protrusion orientations in order to maintain effective attachment in the presence of various directional stresses associated with the absorbent pad while being worn. (For purposes herein, "protrusion orientation" means the directional orientation of a line of protrusions within a protrusion island, such as the lines of protrusions shown in FIG. 17A, relative to the longitudinal axis of the elongated pad. In the case of FIG. 17A, there is a single protrusion orientation that is parallel with the major axis of the oval protrusion island.) Returning to the pad shown in FIG. 18, it has three oval protrusion islands at each end of the pad arranged in an arc. Each oval protrusion island has a different protrusion orientation since the major axis of each of the ovals is aligned differently. For the circular protrusion islands C, it is believed advantageous to align the protrusions in at least one of the protrusion islands with the lengthwise direction of the pad and align the protrusions in at least one other protrusion island with the widthwise direction of the pad. The third circular protrusion island may optionally, for example, be oriented at a 45 degree angle to the lengthwise direction of the pad. Accordingly, the number of protrusion orientations within a pad can be 1 or more, suitably 2 or more, more specifically from 2 to about 30, more specifically from 2 to about 20, more specifically from about 5 to about 20 and still more specifically from about 10 to about 20. The pad shown in FIG. 18 has at least 6 protrusion orientations, excluding the orientation of the circular protrusion islands.

In addition, it is believed that the use of a large number of relatively small protrusion islands is preferable to a relatively few, but larger protrusion islands. Such an arrangement provides more numerous spaces between the protrusion islands which enables the pad to flex and minimize stresses on the attachment area to prevent the attachments from disengaging (snapping off) due to stresses from the undergarment, absorbent article and the body movement during use.

The number of protrusion islands positioned at the ends of the pad will depend, as previously mentioned, on many factors. Nevertheless, in general, a suitable number of protrusion islands at the ends of the pad can be from 1 to about 15, more specifically from 2 to about 10 and still more specifically from about 3 to about 5. Similarly, the number of protrusion islands positioned on each side of the pad near the center of the pad can suitably be from 1 to about 30, more specifically from about 2 to about 20, more specifically from about 3 to about 15 and still more specifically from 3 to about 12.

The location of the protrusion islands at the ends of the pad can vary. In general, there are three available locations. One location is between the edge 36 of the pad and the edge 34 of the absorbent core. Another location is inside (toward the center of the pad) the edge of the absorbent core. The third location is in between, such that the protrusion islands overlap the absorbent core edge. The latter situation is illustrated in FIG. 18, which can be advantageous because the presence of the protrusion islands at this point can soften the stress differential created by the edge. However, it can be particularly advantageous to place the protrusion islands between the edge of the pad and the edge of the absorbent core since the backsheet material is more flexible and forgiving, which aids in maintaining attachment.

As mentioned earlier, the protrusions may be formed on a backing material. Accordingly, a convenient method of applying the protrusion islands is to simply adhere them to the backsheet of the pad. The desired pattern of the protrusion islands may be formed on the backing material, which can be applied to the backsheet of the pad, or the individual protrusion islands can be cut from a sheet of the backing material and adhered to the backsheet in the desired pattern.

FIG. 19 schematically illustrates another embodiment of an absorbent pad in accordance with this invention, in which each end of the pad is provided with 5 oval protrusion islands of type "A" positioned in an arc and the central sides of the pad are provided with three vertical rows of oval protrusion islands oriented at an angle, the middle row consisting of type "A" protrusion islands and the other two rows consisting of type "B" protrusions. The pad of this figure has 12 protrusion orientations.

FIG. 20 schematically illustrates another embodiment of an absorbent pad in accordance with this invention, wherein the ends of the pad are provided with 3 oval type "A" protrusion islands and the central sides of the pad are provided with four diagonal rows of type "A" protrusions. The pad of this figure has 8 protrusion orientations.

As will be appreciated by those skilled in the art, there are many, many different possible attachment combinations within the scope of this invention.

EXAMPLES

Example 1

It may be desirable that the spatial parameters of the protrusions 23 of the male component 20 of the present invention, such as their cross-sectional dimensions, length, height and surface density be designed taking in the account properties of the targeted female component 22 or a group of targeted female components 22.

The samples of materials taken from feminine undergarments analyzed were:
1. Samples of black knitted nylon material, commercially available under the trade designation of "non-cling Tricot 40 denier Antron III sanitized", purchased from Kieffer's Company, located at P.O. Box 719, Jersey City, N.J., 07307.
2. Samples of 100% black cotton jersey, commercially available under the style/color number 0808-6175 and weight of 6.85 ounce per sq. yard, purchased. Samples from Dyersburg Fabric Inc., located at Dyersburg, Tenn., 38024.
3. Samples of beige satin material taken from various regions of the high-cut Satin ladies briefs sold under Vanity Fair® of the Vanity Fair Corporation located at 105 Corporate Center Blvd., Greensboro, N.C., 27408. Briefs were purchased through the J.C. Penney Company.
4. Samples of blue microfiber material taken from various regions of the high-cut microfiber ladies briefs sold under Vanity Fair® of the Vanity Fair Corporation located at 105 Corporate Center Blvd., Greensboro, N.C., 27408. Briefs were purchased through the J.C. Penney Company.

The samples of the materials represent typical types of materials used in feminine undergarments. The samples of the materials represent different types of fibers (synthetic and natural) and different types of weaves (less dense, such as the cotton jersey sample of material and more dense, such as the satin sample of material).

The following undergarment material parameters were obtained as discussed below:
1. Average pore sizes
2. Pore size distribution
3. Pore density
4. Weave pattern
5. Average material thickness These parameters were used to establish suitable dimensions for protrusions 23 of a male component 20 capable of engaging materials typically used in feminine undergarments.

Determination of the pore dimensions, pore density, and weave pattern were made by analysis of micro-images of undergarment samples of the materials. The micro-images were obtained using the high-resolution Keyence® Digital Microscope VH-6300 commercially available from Keyence Corporation located at 1-3-14, Higashi-Nakajima, Higashi-Yodogawa-ku, Osaka, 533, Japan. The micro-images were obtained using a magnification of 50× for the pore density determination, and a magnification of 175× for the pore size determination. All measurements were taken while the samples of material were experiencing no stress or elongation forces.

The pore size determination of each sample of material was accomplished using the "Measure" option on the controller unit of the microscope. Before each measurement, a calibration of distance was performed for measurement accuracy. To measure the size of a pore, a Keyence® VH-6300 Camera unit (complimentary to the Keyence® Digital Microscope) was focused on the sample of material being analyzed so that the image of the sample was displayed clearly on the monitor screen. A pore region was then secluded by a polygon shape outlining the shape of the pore region being measured. Measurement of the polygon area was performed by using "Area" option on the controller menu of the microscope. The measurement was repeated at least 50 times. At least three pieces of each sample of material were used for measurement, from different regions of the sample of material. An average value of the measurements was calculated. For simplification of the calculations, different polygon shapes representing different pore shapes were approximated by circles of equal area, and the circle diameter was used as a parameter characterizing pore size of any particular pore. FREQUENCY function in Excel® software (a part of the standard Microsoft Office Software Package) was used to analyze pore sizes distribution.

The determinations of pore density and weave pattern of each sample of material was accomplished using micro-images of 50× magnification. The micro-images were made using the high-resolution Keyence® Digital Microscope VH-6300. The "X-Y distance" option on a controller menu was used to determine the distances between the adjacent pores in X and Y directions of each sample of material. The measurement was repeated at least 15 times. At least three pieces of each sample of material were used for measurement, from up to 5 different regions of the sample of material. An average value of the measurements was calculated. Standard deviations were calculated using Excel®.

The thickness of each sample of material was measured using digital thickness tester from SONY at 1.38 kPa. The measurement was repeated at least 15 times. At least three pieces of each sample of material were used for measurement, from up to 5 different regions of the sample of material. An average value of the measurements was calculated.

Figure 12:
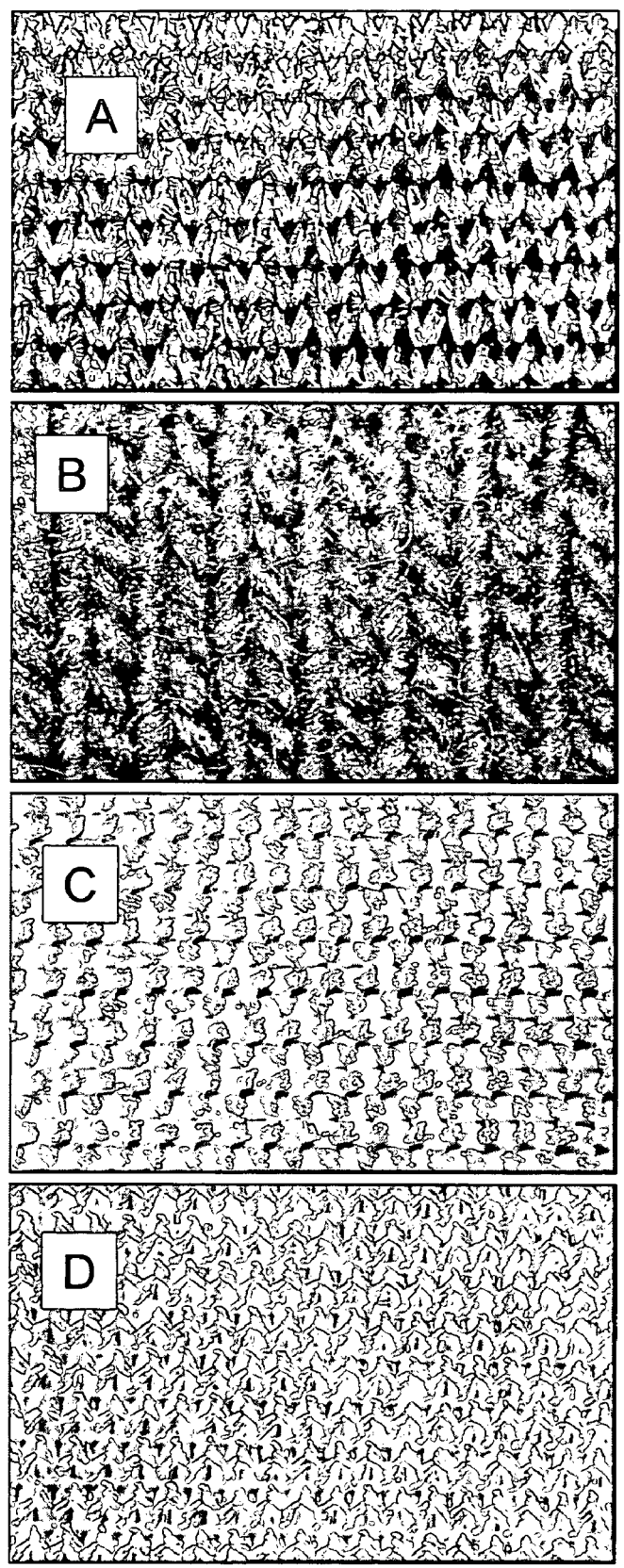
FIGS. 12a-12d are microphotographs of some loop materials at a magnification of 50×.
Figure 15A:
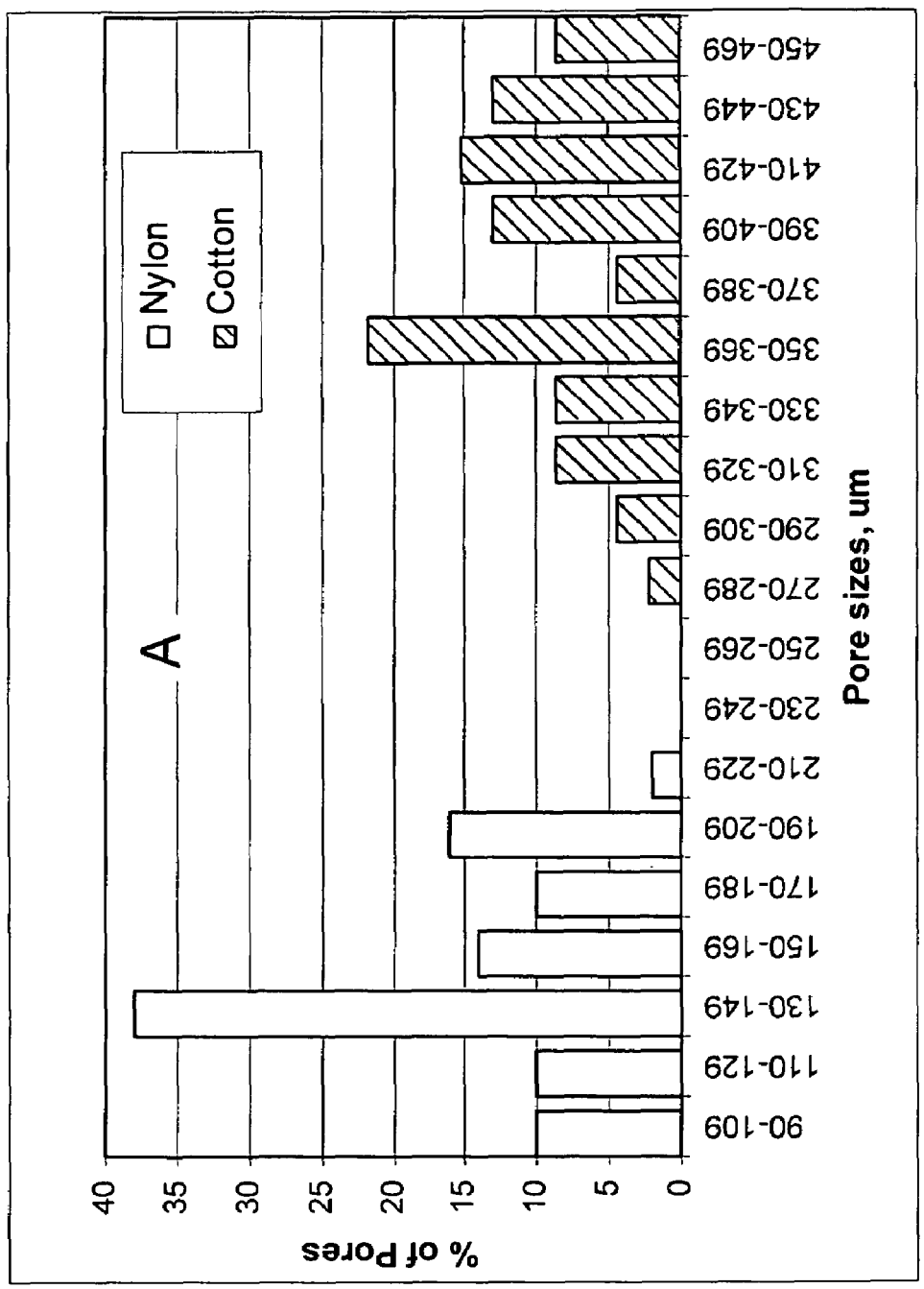
FIGS. 15a-15c are bar graphs showing of pore size distributions of loop materials.
Figure 15B:
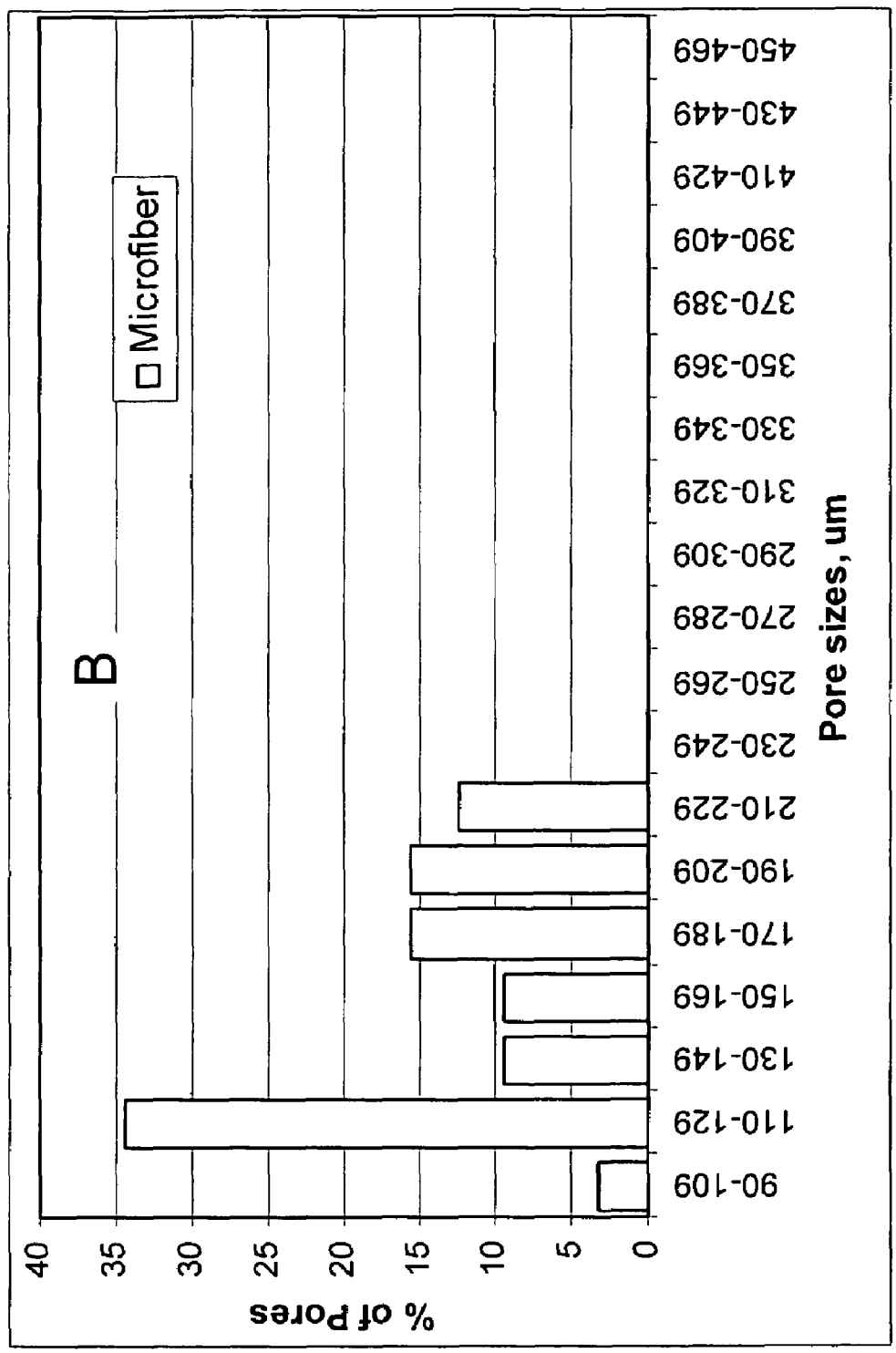
Figure 15C:
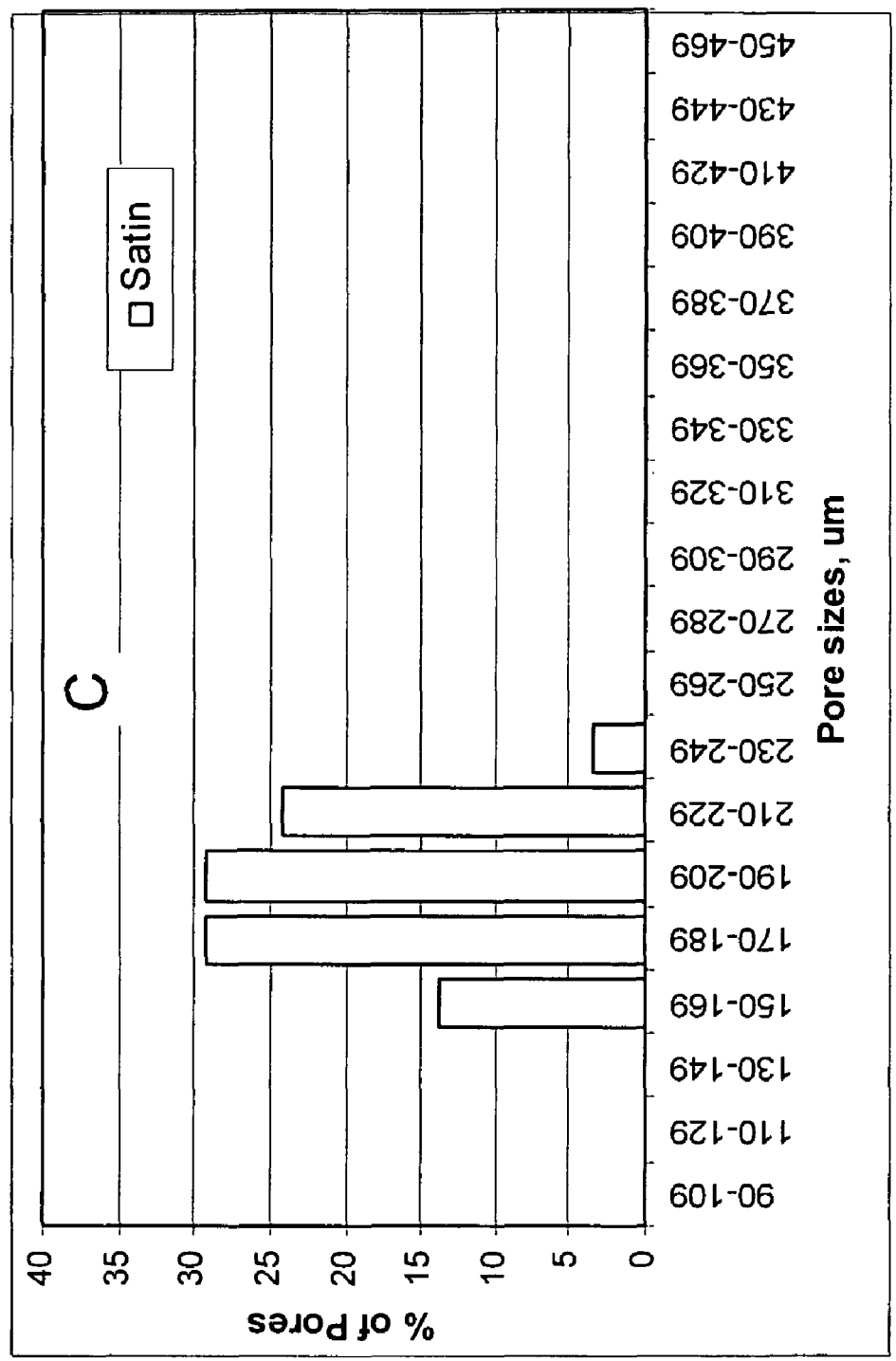
Figure 16A:
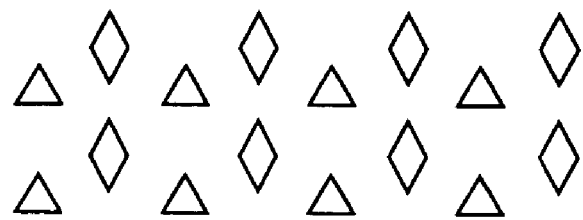
FIGS. 16a-16d are schematic drawings of void patterns of loop materials.
Figure 16B:
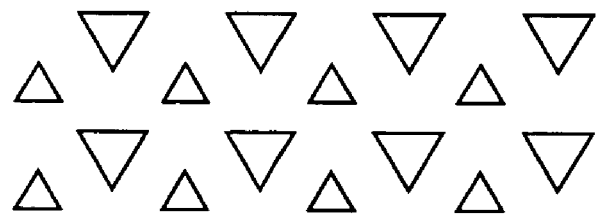
Figure 16C:
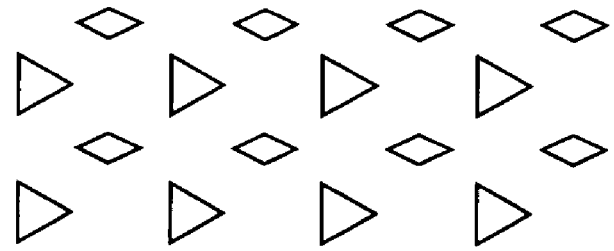
Figure 16D:
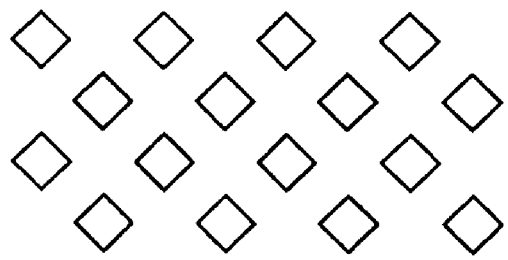

FIGS. 15a-15c show the pore size distributions for the different types of materials, cotton, nylon, microfiber and satin. The cotton, nylon, and microfiber materials were all showing broad bi-modal distributions of pore sizes, reflecting the fact that these materials, with a complex weave pattern, had two types of pores, large and small (as shown in FIGS. 16a-16d). The satin material showed a more uniform unimodal pore size distribution consistent with its more uniform weave pattern (see FIG. 12 and FIG. 16d). The average pore sizes for all four materials are summarized in Table 1.

Differences in weave patterns of different materials are more easily observed in the microphotographs of the materials presented in FIGS. 12a-12d. FIG. 12a is a microphotograph of the nylon sample of material. FIG. 12b is a microphotograph of the cotton sample of material. FIG. 12c is a microphotograph of the microfiber sample of material. FIG. 12d is a microphotograph of the satin sample of material. The weave patterns of the four samples of material were different. The weave pattern of the cotton sample of material was the least dense and the weave pattern of the satin sample of material was the most dense. The cotton sample of material also exhibited a higher degree of 'fuzziness' due to single fibers projecting from the yarns. Schematic drawings of void patterns for the four samples of the materials are shown in FIGS. 16a-16d. To quantify densities of the weave patterns of the four samples of materials, the number of pores per square inch was determined for each sample. The determination was accomplished by measuring average distances between the adjacent pores in both the MD and CD directions. The average pore densities are provided in Table 1. Densities of the samples of materials as determined are: Cotton<Microfiber≦Nylon<Satin. The cotton sample of material was about 2.5 times less dense than the microfiber sample of material, while the satin sample of material was about 2.7 times more dense than the nylon sample of material.

The results of the thickness determination of the samples of the materials are also provided in Table 1.

TABLE 1

|  | Nylon | Cotton | Microfiber | Satin |
| --- | --- | --- | --- | --- |
| Pore Sizes |  |  |  |  |
| Ave. Dia., μm | 150 | 380 | 158 | 196 |
| Min. Dia., μm | 93 | 280 | 107 | 151 |
| Max. Dia., μm | 228 | 462 | 226 | 239 |
| Stnd dev., μm | 31 | 48 | 38 | 21 |
| AVE. Distance Between Pores: |  |  |  |  |
| in CD, μm | 545 | 1,022 | 407 | 240 |
| Stnd dev., μm | 20 | 37 | 1 | 2 |
| in MD, μm | 485 | 702 | 706 | 392 |
| Stnd dev., μm | 33 | 15 | 3 | 5 |
| Pore Surface Density |  |  |  |  |
| Ave. density, voids/cm$^2$ | 757 | 279 | 696 | 2,129 |
| Stnd dev., voids/cm$^2$ | 52 | 6 | 3 | 24 |
| Ave. density, voids/inch$^2$ | 4,882 | 1,800 | 4,490 | 13,136 |
| Stnd dev., voids/inch$^2$ | 332 | 38 | 19 | 144 |
| Thickness |  |  |  |  |
| Ave. thickness, μm | 280 | 680 | 300 | 300 |
| Stnd dev., μm | 20 | 20 | 30 | 30 |

Suitable designs and dimensions of the male component 20 capable of engaging with various female components 22 having different pore sizes, pore densities, weave patterns, and thicknesses are described below. Suitable cross-sectional-dimensions of protrusions 23 and 25 of the male component 20 may have comparable cross-sectional dimensions of material voids within the female component 22. If the cross-sectional dimensions of the protrusions 23 and/or 25 of the male component 20 differ significantly from the cross-sectional dimensions of the material voids within the female component 22 (greater or less than), the engagement may fail. If the cross-sectional dimension of the protrusions 23 and/or 25 of the male component is significantly greater than the material voids within the female component 22, the protrusions 23 and/or 25 may not be able to penetrate the female component 22. If the cross-sectional dimension of the protrusions 23 and/or 25 of the male component 20 is significantly less than the material voids within the female component 22, the engagement of the male component 20 and female component 22 may not be able to be maintained during use. The cross-sectional dimensions of protrusions 23 and/or 25 of the male component 20 may be within the range between about 90 μm to about 470 μm, alternatively about 100 μm to about 460 μm, or alternatively about 110 μm to about 450 μm. The lower limit of the cross-sectional dimension of the protrusions 23 and/or 25 of the male component 20 may be independently about 90 μm, about 100 μm, about 110 μm, or about 120 μm. The upper limit of the cross-sectional dimension of the protrusions 23 and/or 25 of the male component 20 may be independently about 440 μm, about 450 μm, about 460 μm, or about 470 μm.

The protrusions 23 and/or 25 of the male component 20 may include a variety of cross-sectional shapes, such as cones, pyramids, tapered cones, tapered pyramids, truncated cones, and the like. Wherein the protrusions 23 and/ 25 have a tapered shape, such protrusions 23 and/or 25 may more easily penetrate or otherwise engage a wider variety of different female components 22 characterized by different pore sizes and other characteristics affecting penetration and engagement by protrusions 23 and/or 25. This may be explained by the varying cross-sectional dimension through the length of the protrusion 23 and/or 25.

In other embodiments of the present invention, the male component 20 may include more than one type of protrusions 23 and/or 25. Each type of protrusions 23 and/or 25 may have cross-sectional dimensions and/or cross-sectional shapes that may be corresponding to a particular range of material voids within a female component 22. As such, the male component 20 may demonstrate improved engagement with a variety of different female components 22. In some embodiments of the present invention, similar protrusions 23 and/or 25 may be positioned within islands, stripes, or other configurations on the surface of the male component 20.

In some embodiments of the present invention, the height of protrusions 23 and/or 25 of the male component 20, as measured from the base to the tip of the protrusions 23 and/or 25 may be less than the thickness of female component 22. Such a configuration of the protrusions 23 and/or 25 may avoid direct skin contact, and thus, skin irritation, with the protrusions 23 and/or 25 of the male component 20. In some embodiments of the present invention, the heights of the protrusions 23 and/or 25 of the male component 20 may be about 250 μm to about 700 μm, alternatively about 280 μm to about 680 μm, or alternatively about 300 μm to about 670 μm. The lower limit of the height of the protrusions 23 and/or 25 of the male component 20 may be independently about 200 μm, about 250 μm, about 275 μm, or about 300 μm. The upper limit of the cross-sectional dimension of the protrusions 23 and/or 25 of the male component 20 may be independently about 700 μm, about 690 μm, about 680 μm, or about 670 μm.

The surface density, the number of protrusions 23 and/or 25 per square centimeter of the male component 20, may range from about 270 prot./cm$^2$ to about 2,200 prot./cm$^2$, alternatively about 290 prot./cm$^2$ to about 2,000 prot./cm$^2$, alternatively about 300 prot./cm$^2$ to about 1,800 prot./cm$^2$, or alternatively about 320 prot./cm$^2$ to about 1,600 prot./cm$^2$. The lower limit of the surface density of the male component 20 may be independently about 250 prot./cm$^2$, about 270 prot./cm$^2$, about 290 prot./cm$^2$, about 300 prot./cm$^2$, or about 320 prot./cm$^2$. The upper limit of the surface density of the male component 20 may be independently about 2,200 prot./cm$^2$, about 2,000 prot./cm$^2$, about 1,800 prot./cm$^2$, or about 1,600 prot./cm$^2$.

Example 2

To illustrate the correlation between the separation forces acting on a mechanical fastener during disengagement and the level of damage to the female component, a testing of the forces experienced by the mechanical fastening system during the disengagement in peel and shear mode was conducted. Tests were conducted using a standard tensile frame Model Number Sintech I/S, serial No. 7190, equipped with TestWorks for Windows software from MTS Systems Corporation located at P.O. Box 24012, Minneapolis, Minn., 55424, in accordance with the manufacturer's manual. The 50 N transducer was used together with the tensile frame to measure forces, and the instrument was calibrated for this transducer before each test. The loop material was in the form of knitted nylon material, commercially available under the trade designation "non-cling Tricot 40 denier Antron III sanitized", manufacturer part number 4500 T "Antron" III, purchased from Kieffer's Co. located at P.O. Box 719, Jersey City, N.J., 07307. The material was cut in 2"×8" (51 mm×203 mm) samples for the peel test. For the purpose of repeatability of the force measurements, male component was always engaged to the loop material by rolling the sample with a mechanical roll-down unit providing a pressure of 2 kg twice at a speed of 4.9 mm/s. The material was peeled from the male component of a mechanical fastener at a 180-degree angle and at a peel speed of 20 inches/minute (8.47 mm/s)and the resulting peel force was recorded. In a separate series of tests, the material was separated from the male component in sheer mode at a speed of 20 inch/minute (8.47 mm/s) and the resulting sheer force was recorded.

TABLE 2

Average peel forces measured during disengagement of the male component 20 from the female component 23 by peel forces and resulting levels of loop damage.

| No. | Code name | Average force during disengagement by peel, N/m | Level of damage to the loop material |
|---|---|---|---|
| 1 | 100-7003 | 2.3 | No |
| 2 | 102-7004 | 3.9 | No |
| 3 | 102-7003 | 4.6 | No |
| 4 | 100-7005 | 5.2 | No |
| 5 | 102-1002 | 7.4 | No |
| 6 | 61-1036 | 7.7 | No |
| 7 | 102-7006 | 9.4 | no |
| 8 | 100-1001 | 12.3 | no |
| 9 | 61-1035 | 12.7 | no |
| 10 | 102-7005 | 19.0 | no |
| 11 | 103-7005 | 22.8 | slight |
| 12 | 103-1001 | 24.7 | slight |
| 13 | 102-1001 | 47.8 | moderate |
| 14 | 38-1002 | 235.4 | severe |

| Code | Protrusion Shape | Angle α | Protrusion Density (prot./cm²) | Flexural Modulus (Mpa) |
|---|---|---|---|---|
| 38-1002 | see FIG. 6b | 37° | 182 | |
| 61-1035 | see FIG. 6a | 90° | 455 | 2,034 ± 310 |
| 61-1036 | see FIG. 6a | 90° | 455 | |
| 100-1001 | see FIG. 6b | 60° | 672 | 2,034 ± 310 |
| 100-7003 | see FIG. 6b | 60° | 672 | 448 ± 138 |
| 100-7005 | see FIG. 6b | 60° | 672 | 1,172 ± 207 |
| 102-1001 | see FIG. 6b | 60° | 336 | 2,034 ± 310 |
| 102-1002 | see FIG. 6b | 75° | 336 | 2,034 ± 310 |
| 102-7003 | see FIG. 6b | 60° | 336 | 448 ± 138 |
| 102-7004 | see FIG. 6b | 75° | 336 | 448 ± 138 |
| 102-7005 | see FIG. 6b | 60° | 336 | 1,172 ± 207 |
| 102-7006 | see FIG. 6b | 75° | 336 | 1,172 ± 207 |
| 103-1001 | see FIG. 6a | 60° | 336 | 2,034 ± 310 |
| 103-7005 | see FIG. 6a | 60° | 336 | 1,172 ± 207 |

Figure 13:
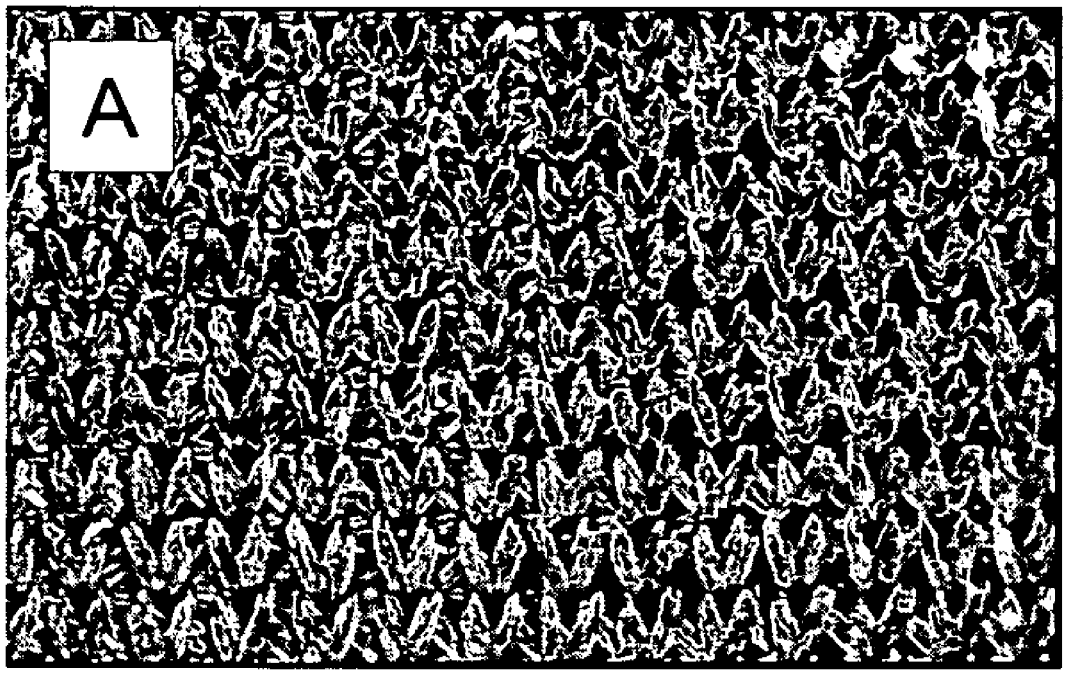
FIG. 13a is a microphotograph of loop material before the engagement of a conventional hook material.
FIG. 13b is a microphotograph of loop material after the engagement of a conventional hook material and subsequent disengagement of the conventional hook material.
Figure 13:
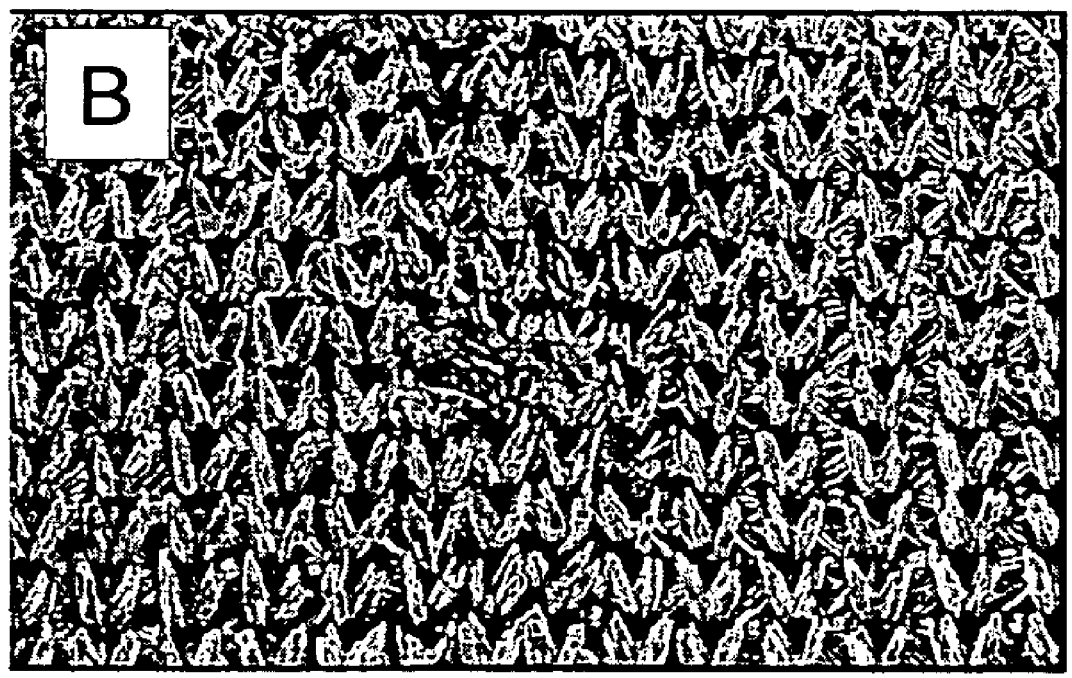
Figure 14B:
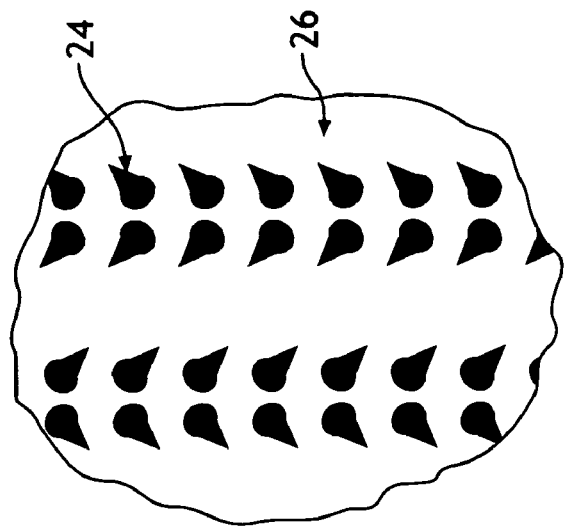
FIGS. 14a-14b are top plan views of portions of a male component of mechanical fastener with angled protrusions.
Figure 14D:
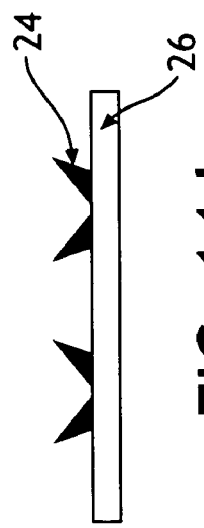
FIGS. 14c-14d are side views of portions of a male component of mechanical fastener with angled protrusions.
Figure 14A:
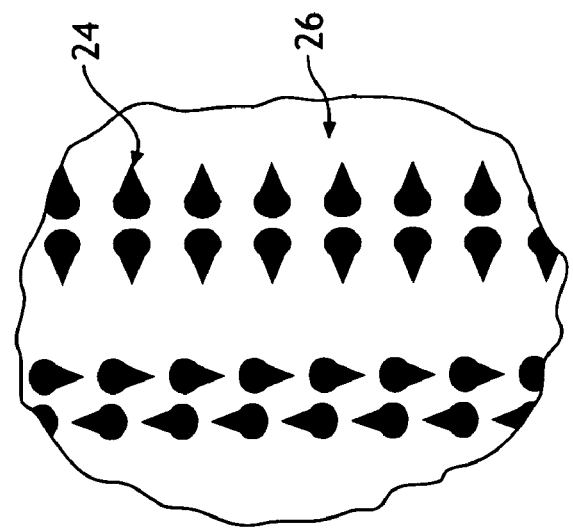
Figure 14C:
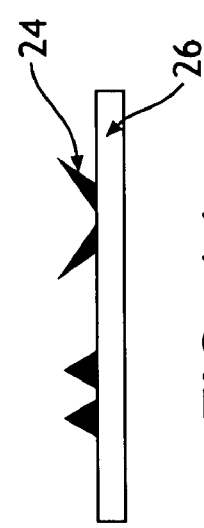

As shown in Table 2, the loop material 30 did not experience any damage if the average peel force during disengagement was lower than about 22.8 N/m. It was further demonstrated that when the average peel force was above about 22.8 N/m but below about 47.8 N/m only a slight impact on the loop material 30 was observed resulting in a slight increase of fuzziness of the surface of the loop material 30. However when the average peel force during disengagement was about 47.8 N/m or higher, a moderate amount of damage to the loop material 30 was observed resulting in a noticeable string-out and fiber pull-out, and a significant increase of fuzziness of the surface of the loop material 30, so that the area where a male component 20 was attached became clearly noticeable and different in appearance from the rest of the female component 22. It was further demonstrated that when the average peel force reached the level of about 235.4 N/m or higher, a severe damage to the female component 22 was observed. The level of damage was comparable to the damage caused to the loop material 30 by the conventional hook material as demonstrated in FIGS. 13a-13b.

It is to be understood that the present invention is aimed at the male component 20 of the mechanical fastener that can only cause no impact or slight impact on the female component 22. Thus, the male component 20 of the present invention may exert a peel force on a nylon female component 22 that ranges from about 0.2 N/m to about 47.8 N/m, alternatively about 0.4 N/m to about 47.5 N/m, alternatively about 0.8 N/m to about 47.1 N/m, or alternatively about 2.3 N/m to about 46.3 N/m. The lower limit of the peel force may be independently about 0.2 N/m, about 0.4 N/m, about 0.8 N/m, or about 2.3 N/m. The upper limit of the peel force may be independently about 46.3 N/m, about 47.1 N/m, about 47.5 N/m, or about 47.8 N/m.

Table 3 provides data of the shear forces measured during the separation of the male component 20 from the female component 22 in the shear mode. The female component 22 was the sample of material of nylon. No significant damage, as discussed above, was recorded during the separation of the male component 20 from the female component 22 under the application of peel force. In some embodiments of the present invention, the shear force during the separation of the male component 20 from the female component 22 in the shear mode may be in the range from about $6.08 \times 10^3$ N/m² to about $2.43 \times 10^4$ N/m², alternatively about $6.38 \times 10^3$ N/m² to about $2.42 \times 10^4$ N/m², alternativley about $6.68 \times 10^3$ N/m² to about $2.40 \times 10^4$ N/m², or alternatively about $7.00 \times 10^3$ N/m² to about $2.34 \times 10^4$ N/m². The lower limit of the peel force may be independently about $6.08 \times 10^3$ N/m², about $6.38 \times 10^3$ N/m², about $6.68 \times 10^3$ N/m², or about $7.00 \times 10^3$ N/m². The upper limit of the peel force may be independently about $2.43 \times 10^4$ N/m², about $2.42 \times 10^4$ N/m², about $2.40 \times 10^4$ N/m², or about $2.34 \times 10^4$ N/m².

TABLE 3

Average Shear Forces Measured during Disengagement of the Male Component 20 from the Female Component 23 Shear Mode.

| No. | Code name | Average force during disengagement by shear, N/m² |
|---|---|---|
| 1 | 100-7003 | $6.38 \times 10^3$ |
| 2 | 102-7004 | $4.56 \times 10^3$ |
| 3 | 102-7003 | $6.99 \times 10^3$ |
| 4 | 100-7005 | $2.28 \times 10^4$ |
| 5 | 102-1002 | $1.28 \times 10^4$ |
| 6 | 61-1036 | $7.29 \times 10^3$ |
| 7 | 102-7006 | $1.73 \times 10^4$ |
| 8 | 100-1001 | $1.73 \times 10^4$ |
| 9 | 61-1035 | $1.99 \times 10^4$ |
| 10 | 102-7005 | $2.37 \times 10^4$ |
| 11 | 103-7005 | $2.64 \times 10^4$ |
| 12 | 103-1001 | $2.34 \times 10^4$ |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An elongated absorbent pad having two ends, two side edges, an absorbent surface for contacting the body of a user and a backsheet with a back surface for contacting the clothing of the user, said back surface having one or more protrusion islands positioned within each end of the pad and one or more protrusion islands centrally positioned inside each of the side edges of the pad for attaching the absorbent pad to the clothing of the user, wherein each protrusion island has a size of from about 5 to about 100 square millimeters and contains a plurality of outwardly extending first protrusions and a plurality of outwardly extending second protrusions, said first and second protrusions within each protrusion island being oriented differently from each other and pointing in opposite directions, said protrusions having a height from about 0.003 centimeters to about 0.9 centimeters and a Flexural Modulus from about 331 MPa to about 2,758 MPa, wherein the first protrusions extend at an angle from about 5 degrees to about 85 degrees relative to the back surface and the second protrusions extend at an angle from about 95 degrees to about 175 degrees relative to the back surface.

2. The absorbent pad of claim 1, wherein the protrusion islands contain about the same number of first protrusions and second protrusions.

3. The absorbent pad of claim 1 wherein the first protrusions and the second protrusions are arranged within the protrusion islands in alternating rows.

4. The absorbent pad of claim 1 having an absorbent core and an absorbent core edge positioned inside the outer edges of the ends of the pad, wherein the one or more protrusion islands positioned within each end of the pad are positioned between the absorbent core edge and the outer edge of the end of the pad.

5. The absorbent pad of claim 1 having an absorbent core and an absorbent core edge positioned inside the outer edges of the ends of the pad, wherein the one or more protrusion islands positioned within each end of the pad overlap the absorbent core edge.

6. The absorbent pad of claim 1 having an absorbent core and an absorbent core edge positioned inside the outer edges of the ends of the pad, wherein the one or more protrusion islands positioned within each end of the pad are positioned inside the absorbent core edge.

7. The absorbent pad of claim 1 having 3 or more protrusion islands positioned within each end of the pad and arranged in an arc, wherein the first protrusions and the second protrusions within each protrusion island are arranged in alternating rows and wherein the protrusion islands are oriented such that the rows of protrusions within each protrusion island are not parallel to the rows of protrusions in the other protrusion islands.

8. The absorbent pad of claim 1 wherein the number of protrusion islands positioned at each end of the pad is from 1 to about 15.

9. The absorbent pad of claim 1 wherein the number of protrusion islands positioned at each end of the pad is from 2 to about 10.

10. The absorbent pad of claim 1 wherein the number of protrusion islands positioned at each end of the pad is from 3 to about 5.

11. The absorbent pad of claim 1 wherein the number of protrusion islands positioned on each side of the pad near the center of the pad is from 1 to about 30.

12. The absorbent pad of claim 1 wherein the number of protrusion islands positioned on each side of the pad near the center of the pad is from 2 to about 20.

13. The absorbent pad of claim 1 wherein the number of protrusion islands positioned on each side of the pad near the center of the pad is from 3 to about 15.

14. The absorbent pad of claim 1 wherein the number of protrusion islands positioned on each side of the pad near the center of the pad is from 3 to about 12.

15. The absorbent pad of claim 1 wherein the number of protrusion orientations is 2 or more.

* * * * *